US008920797B2

(12) United States Patent
Igawa et al.

(10) Patent No.: US 8,920,797 B2
(45) Date of Patent: Dec. 30, 2014

(54) HIGHLY CONCENTRATED STABILIZED IGM SOLUTION

(75) Inventors: Tomoyuki Igawa, Shizuoka (JP); Yasuo Sekimori, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 1208 days.

(21) Appl. No.: 12/509,075

(22) Filed: Jul. 24, 2009

(65) Prior Publication Data

US 2009/0285802 A1     Nov. 19, 2009

Related U.S. Application Data

(63) Continuation of application No. 10/575,192, filed as application No. PCT/JP2004/014935 on Oct. 8, 2004, now abandoned.

(30) Foreign Application Priority Data

Oct. 9, 2003  (JP) ................................. 2003-351388

(51) Int. Cl.
*A61K 39/395* (2006.01)
*C07K 16/30* (2006.01)
*A61K 47/02* (2006.01)
*A61K 47/18* (2006.01)
*A61K 47/12* (2006.01)
*A61K 31/7016* (2006.01)
*A61K 47/26* (2006.01)
*A61K 31/198* (2006.01)
*A61K 9/00* (2006.01)

(52) U.S. Cl.
CPC ........... *C07K 16/3084* (2013.01); *A61K 9/0095* (2013.01); *A61K 47/02* (2013.01); *A61K 47/18* (2013.01); *A61K 47/12* (2013.01); *A61K 31/7016* (2013.01); *A61K 39/39558* (2013.01); *C07K 2317/21* (2013.01); *A61K 47/26* (2013.01); *A61K 47/183* (2013.01); *A61K 9/0019* (2013.01); *A61K 39/39591* (2013.01); *A61K 31/198* (2013.01); *C07K 2317/52* (2013.01)
USPC ..................................................... 424/130.1

(58) Field of Classification Search
None
See application file for complete search history.

(56) References Cited

U.S. PATENT DOCUMENTS

| | | | |
|---|---|---|---|
| 5,157,113 A | 10/1992 | Dove et al. | |
| 5,190,752 A | 3/1993 | Möller et al. | |
| 5,547,853 A | 8/1996 | Wallner et al. | |
| 5,792,838 A | 8/1998 | Smith et al. | |
| 5,830,470 A | 11/1998 | Nakamura et al. | |
| 5,908,826 A | 6/1999 | Fukuda et al. | |
| 6,136,312 A | 10/2000 | Rentsch | |
| 6,238,891 B1 | 5/2001 | Maiorella et al. | |
| 8,257,703 B2 | 9/2012 | Irie et al. | |
| 2002/0119530 A1 | 8/2002 | Maiorella et al. | |
| 2004/0081972 A1 | 4/2004 | Satoh et al. | |
| 2004/0170623 A1 | 9/2004 | Arvinte et al. | |
| 2005/0118167 A1 | 6/2005 | Okada et al. | |
| 2006/0127395 A1 | 6/2006 | Arvinte et al. | |
| 2007/0154469 A1 | 7/2007 | Irie | |
| 2007/0212346 A1 | 9/2007 | Igawa et al. | |
| 2007/0249812 A1 | 10/2007 | Hayasaka et al. | |
| 2010/0172899 A1 | 7/2010 | Irie et al. | |

FOREIGN PATENT DOCUMENTS

| | | |
|---|---|---|
| CA | 2057842 A1 | 6/1992 |
| EP | 0 352 500 | 1/1990 |
| EP | 0 492 409 | 7/1992 |
| EP | 0531539 A1 | 3/1993 |
| EP | 1 174 148 | 1/2002 |
| EP | 1 176 195 | 1/2002 |
| EP | 0841067 B1 | 5/2002 |
| EP | 1226752 A1 | 7/2002 |
| JP | 2-000493 | 1/1990 |
| JP | 2-078635 | 3/1990 |
| JP | 2501116 A | 4/1990 |
| JP | 04-360696 | 12/1992 |
| JP | 5-065233 | 3/1993 |
| JP | 5192181 A | 8/1993 |
| JP | 6178689 A | 6/1994 |
| JP | 6-189781 | 7/1994 |
| JP | 6-205694 | 7/1994 |
| JP | 7-502497 | 3/1995 |
| JP | 9-127112 | 5/1997 |
| JP | 9-127114 | 5/1997 |
| JP | 10324699 A | 12/1998 |
| JP | 2000154149 A | 6/2000 |
| JP | 2000516470 A | 12/2000 |
| JP | 2001-504092 | 3/2001 |
| JP | 2002037800 A | 2/2002 |
| JP | 2002504342 A | 2/2002 |
| JP | 2002509122 A | 3/2002 |
| JP | 2002527100 A | 8/2002 |
| JP | 2003128576 A | 5/2003 |
| WO | WO 89/01975 | 3/1989 |
| WO | WO 89/04867 | 6/1989 |

(Continued)

OTHER PUBLICATIONS

Okada, "Preparation of IgM Antibody-Producing Cell Lines that React to HIV-Infected Cell Lines," Japan Health Science Foundation, 108-110 (1998).

(Continued)

*Primary Examiner* — Sharon Wen

(74) *Attorney, Agent, or Firm* — Fish & Richardson P.C.

(57) ABSTRACT

The present inventors discovered that stable and highly concentrated IgM solutions can be prepared by using, as an additive, a compound comprising a polyvalent cationic ion, such as magnesium chloride or arginine hydrochloride, to suppress IgM aggregation in solutions.

21 Claims, 6 Drawing Sheets

(56) References Cited

FOREIGN PATENT DOCUMENTS

| WO | WO 91/18106 | 11/1991 |
|---|---|---|
| WO | WO 93/08837 | 5/1993 |
| WO | 9419457 | 9/1994 |
| WO | WO9806749 A2 | 2/1998 |
| WO | WO 99/01556 | 1/1999 |
| WO | WO 99/37329 | 7/1999 |
| WO | WO9936105 A2 | 7/1999 |
| WO | WO9942597 A1 | 8/1999 |
| WO | WO0023472 A2 | 4/2000 |
| WO | WO 00/61739 | 10/2000 |
| WO | WO 00/66160 | 11/2000 |
| WO | WO 01/23431 | 4/2001 |
| WO | WO0133957 A1 | 5/2001 |
| WO | WO0177342 A1 | 10/2001 |
| WO | WO0210371 A1 | 2/2002 |
| WO | WO 02/096457 | 12/2002 |
| WO | WO 03/046162 | 6/2003 |
| WO | 2005005636 A1 | 1/2005 |
| WO | WO 2005/005636 | 1/2005 |
| WO | 2005035573 A1 | 4/2005 |
| WO | 2005035574 A1 | 4/2005 |
| WO | WO 2005/035573 | 4/2005 |
| WO | WO 2005/035574 | 4/2005 |

OTHER PUBLICATIONS

Fish & Richardson P.C., Amendment in Reply to Action dated Oct. 13, 2011 in U.S. Appl. No. 12/727,162, filed Apr. 12, 2012, 14 pages.
USPTO Notice of Allowance in U.S. Appl. No. 12/727,162, dated Apr. 20, 2012, 5 pages.
USPTO Notice of Allowance in U.S. Appl. No. 12/727,162, dated Jun. 1, 2012, 2 pages.
Matsuuchi et al., "Immunoglobulin J chain gene from the mouse," *Proc. Natl. Acad. Sci. U.S.A.*, 83(2):456-60 (1986).
Azuma et al., "Recombinant Human Hexamer-Dominant IgM Monoclonal Antibody to Ganglioside GM3 for Treatment of Melanoma," Clin. Cancer Res., 13(9):2745-2750 (2007).
Irie et al., "Human Monoclonal Antibody to Ganglioside GM2 for Melanoma Treatment," Lancet, 1(8641):786-787 (1989).
Nishinaka et al., "Development of a Human Monoclonal Antibody for Ganglioside GM2 with Potential for Cancer Treatment," Cancer Research, 56(24):5666-5671 (1996).
Nishinaka et al., "Human IgM antibodies to tumor-associated gangliosides share VHIII (V3-V23) and VKIV family subgroups," Immunogenetics, 48(1):73-75 (1998).
USPTO Notice of Allowance in U.S. Appl. No. 10/564,665, dated Dec. 4, 2009, 11 pages.
European Search Report for App. Ser. No. 10 15 0954, dated May 12, 2010, 5 pages.
Fish & Richardson P.C., Amendment in Reply to Action dated Oct. 22, 2009 in U.S. Appl. No. 10/574,827, filed Jan. 21, 2010, 9 pages.
USPTO Notice of Allowance in U.S. Appl. No. 10/574,827, dated May 4, 2010, 7 pages.
Arya et al., "Mapping of Amino Acid Residues in the Cμ3 Domain of Mouse IgM Important in Macromolecular Assembly and Complement-Dependent Cytolysis," *J. Immun.*, 152:1206-1212 (1994).
Brewer et al., "Mechanism and Subcellular Localization of Secretory IgM Polymer Assembly," *The Journal of Biological Chemistry*, 269(25):17338-17348 (1994).
Cattaneo et al., "Polymeric Immunoglobulin M is Secreted by Transfectants of Non-Lymphoid Cells in the Absence of Immunoglobulin J Chain," *The EMBO Journal*, 6:2753-2758 (1987).
Chen et al.. "Strategies to Suppress Aggregation of Recombinant Keratinocyte Growth Factor During Liquid Formulation Development," *J. Pharm. Sci.*, 83:1657-1661 (1994).
Dráber et al., "Stability of Monoclonal IgM Antibodies Freeze-Dried in the Presence of Trehalose," *Journal of Immunological Methods*, 181:37-43 (1995).
García-González et al., "Purification of Murine IgG3 and IgM Monoclonal Antibodies by Euglobulin Precipitation," *Journal of Immunological Methods*, 111:17-23 (1988).

Gombotz et al., "The Stabilization of a Human IgM Monoclonal Antibody with Poly(vinylpyrrolidone)," *Pharm. Res.* 11:624-632 (1994).
Green, L., "Antibody engineering via genetic engineering of the mouse: XenoMouse strains are a vehicle for the facile generation of therapeutic human monoclonal antibodies," *J. Immun. Methods*, 231:11-23 (1999).
Haruta et al., "Class-Switching of the IgM Type Anit-Adenocarcinoma Human Antibody HB4C5 into an IgG1 Type Resulted in the Loss of the Antigen Binding Ability," *Human Antibodies*, 8:137-145 (1997).
Hoon et al., "Molecular cloning of a human monoclonal antibody reactive to ganglioside GM3 antigen on human cancers," *Cancer Res.*, 53:5244-5250 (1993).
Huang et al., "Production of Recombinant Murine-Human Chimeric IgM and IgG Anti-Js$^b$ for Use in the Clinical Laboratory," *Transfusion*, 43:758-764 (2003).
Hughey et al., "Production of IgM Hexamers by Normal and Autoimmune B Cells: Implications for the Physiologic Role of Hexameric IgM," *J. Immunol.*, 161:4091-4097 (1998).
Irie et al., "Phase I pilot clinical trial of human IgM monoclonal antibody to ganglioside GM3 in patients with metastatic melanoma," *Cancer Immunol. Immunother.*, 53:110-117 (2004).
Jones et al., "Replacing the complementarity-determining regions in a human antibody with those from a mouse," *Nature*, 321:522-525 (1986).
Kallemuchikkal et al., "Evaluation of cryoglobulins," *Arch. Pathol. Lab. Med.*, 123:119-125 (1999).
Kunert et al., "Characterization of Molecular Features, Antigen-Binding, and in Vitro Properties of IgG and IgM Variants of 4E10, an Anti-HIV Type 1 Neutralizing Monoclonal Antibody," *Aids Research and Human Retroviruses*, 20:755-762 (2004).
Mayus et al., "Inhibition of in Vitro Anti-DNA B-Cell Responses by Cyclosporine," *Cell. Immunol.*, 94:195-204 (1985).
Meng et al., "J Chain Deficiency in Human IgM Monoclonal Antibodies Produced by Epstein-Barr Virus-Transformed B Lymphocytes," *Eur. J. Immunol.*, 20:2505-2508 (1990).
Middaugh et al., "Effect of solutes on the cold-induced insolubility of monoclonal cryoimmunoglobulins," *J. Biol. Chem.*, 252:8002-06 (1977).
Middaugh et al., "Molecular basis for the temperature-dependent insolubility of cryoglobulins. IV. Structural studies of the IgM monoclonal cryoglobulin McE," *Immunochem.*, 15:171-187 (1978).
Molina et al., "The Effects of Divalent Cations in the Presence of Phosphate, Citrate and Chloride on the Aggregation of Soy Protein Isolate," *Food Research International*, 32:135-143 (1999).
Monica et al., "Comparative Biochemical Characterization of a Human IgM Produced in Both Ascites and in vitro Cell Culture," *Biotechnology*, 4:512-515 (1993).
Morrison et al., "Chimeric human antibody molecules: Mouse antigen-binding domains with human constant region domains," *Proc. Natl. Acad. Sci. USA*, 81:6851-55 (1984).
Nifong et al., "Separation of IgG and IgM from albumin in citrated human plasma using electrodialysis and metal ion affinity precipitation," *ASAIO J.*, 48:645-649 (2002).
Niles et al., "Polymer IgM Assembly and Secretion in Lymphoid and NonLymphoid Cell Lines: Evidence that J Chain is Required for Pentamer IgM Synthesis," *Proc. Natl. Acad. Sci. USA*, 92:2884-2888 (1995).
Page et al., "Purification of monoclonal antibodies," *Methods Mol. Biol.*, 80:113-119 (1998).
Phillips et al., "Manufacture and quality control of CAMPATH-1 antibodies for clinical trials," *Cytotherapy*, 3:233-242 (2001).
Randall et al., "Direct Evidence That J Chain Regulates the Polymeric Structure of IgM in Antibody-secreting B Cells," *The Journal of Biological Chemistry*, 267(25):18002-18007 (1992).
Randall et al., "J Chain Synthesis and Secretion of Hexameric IgM is Differentially Regulated by Lipopolysaccharide and Interleukin 5," *Proc. Natl. Acad. Sci. USA*, 89:962-966 (1992).
Sharma et al., "Study of IgM Aggregation in Serum of Patients with Macroglobulinemia," *Clin. Chem. Lab. Med.*, 38:759-764 (2000).

(56) References Cited

OTHER PUBLICATIONS

Shitara et al., "Immunoglobulin Class Switch of Anti-Ganglioside Monoclonal Antibody from IgM to IgG," *Journal of Immunological Methods*, 169:83-92 (1994).
Sorensen et al., "Structural Requirements for Incorporation of J Chain into Human IgM and IgA," *International Immunology*, 12(1):19-27 (2000).
Steinbuch et al., "Preparation of an IgM and IgA enriched fraction for clinical use," *Prep. Biochem.*, 3:363-373 (1973).
Stocks et al., "Production and Isolation of Large Quantities of Monoclonal Antibody Using Serum-Free Medium and Fast Protein Liquid Chromatography," *Hybridoma*, 8:241-247 (1989).
Stoll et al., "Effects of culture conditions on the production and quality of monoclonal IgA," *Enzyme Microb. Technol.*, 21:203-211 (1997).
Tachibana, "Gene expression of joining chain in murine peritoneal B-1 cells," *Nihon Univ. Dent. J.*, 76:425-433 (2002) (English abstract included).
Wood et al., "High Level Synthesis of Immunoglobulins in Chinese Hamster Ovary Cells," *The Journal of Immunology*, 145(9):3011-3016 (1990).
Youd et al., "Synergistic roles of IgM and complement in antigen trapping and follicular localization," *Eur. J. Immunol.*, 32:2328-2337 (2002).
USPTO Restriction Requirement U.S. Appl. No. 10/564,665, dated Jul. 9, 2008, 7 pages.
Fish & Richardson P.C., Response to Restriction Requirement dated Jul. 9, 2008, in U.S. Appl. No. 10/564,665, filed Aug. 8, 2008, 1 page.
USPTO Restriction Requirement in U.S. Appl. No. 10/564,665, dated Nov. 12, 2008, 6 pages.
Fish & Richardson P.C., Response to Restriction Requirement dated Nov. 12, 2008, in U.S. Appl. No. 10/564,665, filed Jan. 9, 2009, 1 page.
USPTO Non-Final Office Action in U.S. Appl. No. 10/564,665, dated Apr. 20, 2009, 16 pages.
Japanese Patent Office, International Search Report for App. Ser. No. PCT/JP2004/010444, mailed Oct. 26, 2004, 4 pages.
Japanese Patent Office, International Preliminary Report on Patentability for App. Ser. No. PCT/JP2004/010444, dated Jun. 3, 2005, 5 pages.
USPTO Non-Final Office Action in U.S. Appl. No. 10/574,827, dated Mar. 12, 2008, 11 pages.
Fish & Richardson P.C., Amendment in Reply to Action dated Mar. 12, 2008 in U.S. Appl. No. 10/574,827, filed Sep. 11, 2008, 9 pages.
USPTO Non-Final Office Action in U.S. Appl. No. 10/574,827, dated Dec. 19, 2008, 7 pages.
Fish & Richardson P.C., Amendment in Reply to Action dated Dec. 19, 2008 in U.S. Appl. No. 10/574,827, filed Jun. 18, 2009, 5 pages.
Japanese Patent Office, International Search Report for App. Ser. No. PCT/JP2004/014919, mailed Dec. 7, 2004, 4 pages.
Japanese Patent Office, International Preliminary Report on Patentability for App. Ser. No. PCT/JP2004/014919, dated Sep. 12, 2005, 14 pages.
USPTO Restriction Requirement in U.S. Appl. No. 10/575,192, dated Apr. 15, 2008, 7 pages.
Fish & Richardson P.C., Response to Restriction Requirement dated Apr. 15, 2008 in U.S. Appl. No. 10/575,192, filed Sep. 12, 2008, 1 page.
USPTO Non-Final Office Action in U.S. Appl. No. 10/575,192, dated Jan. 26, 2009, 11 pages.
Japanese Patent Office, International Search Report for App. Ser. No. PCT/JP2004/014935, mailed Jan. 25, 2005, 4 pages.
Japanese Patent Office, International Preliminary Report on Patentability for App. Ser. No. PCT/JP2004/014935, 14 pages.
European Search Report for App. Ser. No. EP 04 79 2204, mailed Jul. 11, 2007, 3 pages.
Shitara et al., "A new vector for the high level expression of chimeric antibodies in myeloma cells," *J. Immunol. Methods.*, 167(1-2):271-8 (1994).
USPTO Non-Final Office Action in U.S. Appl. No. 12/727,162, dated Oct. 13, 2011, 8 pages.
Fish & Richardson P.C., Amendment in Reply to Action dated Apr. 20, 2009 in U.S. Appl. No. 10/564,665, filed Oct. 19, 2009, 6 pages.
USPTO Non-Final Office Action in U.S. Appl. No. 10/574,827, dated Oct. 22, 2009, 8 pages.
European Search Report for App. Ser. No. EP 04 79 2188, dated Sep. 21, 2009, 4 pages.
Brekke & Sandlie, "Therapeutic Antibodies for Human Diseases at the Dawn of the Twenty-First Century," *Nature Reviews Drug Discovery*, 2:52-62 (2003).
Gagnon et al., "Purification of IgM Monoclonal Antibodies," *Biopharm International Supplement Advances in Separation & Purification: Purifying Monoclonal Antibodies* (Mar. 2008).
Janeway CA et al., "The structure of a typical antibody molecule," in *Immunobiology: The Immune System in Health and Disease*, 5th edition, New York: Garland Science (2001). Retrieved from the Internet: <URL: http://www.ncbi.nlm.nih.gov/books/NBK27144/> on Nov. 6, 2013, 4 pages.

HIGHLY CONCENTRATED STABILIZED IGM SOLUTION

CROSS-REFERENCE TO RELATED APPLICATIONS

This application is a continuation application of U.S. patent application Ser. No. 10/575,192, filed Jan. 26, 2007, which is the National Stage of International Application No. PCT/JP2004/014935, filed on Oct. 8, 2004, which claims the benefit of Japanese Patent Application Serial No. 2003-351388, filed on Oct. 9, 2003. The content of the foregoing U.S. application is hereby incorporated by reference in its entirety.

TECHNICAL FIELD

The present invention relates to highly concentrated and stabilized IgM solutions, and production thereof.

BACKGROUND ART

Many higher animals have five different classes of immunoglobulins, IgG, IgA, IgM, IgD, and IgE. Each immunoglobulin class differs in properties such as size, charge, amino acid composition, and sugar content. Of these classes, IgM accounts for approximately 10% of all plasma immunoglobulins. IgM is the major component of early antibodies produced against cell-membrane antigens, infectious microorganisms, or soluble antigens, which have a complex antigenicity.

Human IgMs usually have a pentameric structure. Each of the five subunits constituting this pentameric structure has a four-stranded structure similar to that of IgG. The amino acid sequence of the μ chain, which is the heavy chain of IgM, is different from that of the γ chain, which is the heavy chain of IgG. The following differences can also be seen:

The μ chain has an extra constant domain than the γ chain.
The μ chain has four more oligosaccharide chains than the γ chain.

IgM has a polypeptide chain called the J chain, which is not found in IgG. The J chain is considered to assist the association of μ chains prior to secretion of IgM from antibody producing cells.

With advances in monoclonal antibody technology and recombinant DNA technology, large-scale production of pure immunoglobulins has become possible in recent years. Furthermore, gene recombination techniques have enabled production of chimeric antibodies and humanized antibodies. Chimeric antibodies are antibodies having a structure in which the variable regions have been replaced with variable regions derived from a different species. For example, "chimeric antibodies" comprising variable regions of non-human antibodies and the constant regions of human antibodies (Non-Patent Document 1/Proc. Natl. Acad. Sci. U.S.A., (1984) 81:6851) are known. Also known are humanized antibodies in which the complementarity determining regions (CDR) of other animal species are transferred into human immunoglobulins (Non-Patent Document 2/Nature (1986) 321:521).

Actual examples of antitumor antibodies are the anti-CD20 human chimeric antibody RITUXAN® (IDEC), and the anti-HER2/neu humanized antibody HERCEPTIN® (Genentech), which have completed clinical trials and have already been approved. These antibodies are now commercially available. Antibody-dependent cellular cytotoxicity (hereinafter referred to as ADCC) activity and complement-dependent cytotoxicity (hereinafter referred to as CDC) activity are known as effector functions of IgG and IgM. Since IgM has a higher CDC activity compared to IgG, it has an extremely high chance of becoming an anti-tumor antibody having CDC activity as its main effect. However, as described above, unlike IgG, IgM forms a multimer. Therefore, industrial scale production of recombinant IgM had been considered difficult.

IgM is also very unstable compared to IgG and has a low solubility. Therefore, the production of a highly concentrated and stable IgM solution is difficult. For example, Cytotherapy, 2001, 3(3), 233-242 (Non-Patent Document 5) reports that, even when IgM had been stored at −20° C., precipitation and decrease of activity occurred upon thawing. Furthermore, according to the report, IgM easily aggregates and precipitates during storage. It was especially difficult to ensure an IgM stability sufficient enough to withstand pharmaceutical use only through optimization of pH and buffer type.

Therefore, various attempts are being made to stabilize antibodies by methods other than optimization of pH and buffer type. For example, WO 2002/096457 (Patent Document 1) discloses formulations for stabilizing highly concentrated antibodies that comprise acidic ingredients. This method uses $MgCl_2$ and $CaCl_2$ as additives to stabilize the antibodies, but the stabilization is carried out to prepare IgG formulations, and IgM formulations are not mentioned. As described above, unlike IgG, IgM exists as a multimer, and unlike intrinsically stable IgG, IgM readily aggregates. Therefore, IgM has the distinctive problem of being very difficult to be highly concentrated.

Clin. Chem. Lab. Med. 2000; 38(8): 759-764 (Non-Patent Document 3) and Journal of Immunological Methods, 111 (1988) 17-23 (Non-Patent Document 5) reported that IgM precipitates at a low salt concentration, and redissolves at a high salt concentration in a phosphate buffer and Tris-hydrochloride buffer that are weakly alkaline. Clin. Chem. Lab. Med. 2000; 38(8): 759-764 (Non-Patent Document 3) reports that, near pH 5, IgM readily precipitates and is difficult to handle, suggesting a pessimistic outlook for IgM solutions in weakly acidic buffers. This report thus gives no indication of the possibility of providing a highly concentrated IgM solution as a pharmaceutical or a bulk drug substance. This document also reports that when human sera comprising a high concentration of IgM are diluted with water, insoluble aggregates are generated as euglobulin precipitates, increasing the turbidity of the solution; but when the salt concentration is then raised by adding NaCl, Arginine, or such, the euglobulin precipitates redissolve. However, this report relates to the reconstitution of euglobulin precipitates, and does not provide any disclosures relating to suppression of increase in water-soluble aggregates of IgM. Furthermore, since patient-derived unpurified sera comprising various serum proteins are used in this document, the resulting insoluble aggregates may comprise proteins other than IgM. The effects on IgM solution in the absence of the other proteins are not described.

In Journal of Immunological Methods, 111 (1988) 17-23 (Non-Patent Document 5), a buffer comprising 0.1 M Tris-HCl and 1 M NaCl (pH 8) is used to redissolve euglobulin precipitates. However, the resulting recovery rate of IgM varies from 40% to >90% depending on antibodies or batch, indicating a low reproducibility. Additionally, although the Methods section describes that 5 to 10 mg/mL of purified antibodies were stored at 4° C. and −20° C., the Results section only describes that the antibodies could be stored for a few months at −20° C. without loss of function, and does not mention anything regarding storage at 4° C. or higher, at which temperature it is usually difficult to ensure stability.

Accordingly, this report suggests the difficulty of reproducing precipitate reconstitution and the difficulty of ensuring stability during storage, when trying to provide a highly concentrated solution of IgM as a pharmaceutical product or a bulk drug substance.

BIOTECHNOLOGY 1993, 11, 512-515 (Non-Patent Document 4) and Journal of Immunological Methods, 111 (1988) 17-23 (Non-Patent Document 5) also describe the reconstitution of insoluble aggregates of antibodies as euglobulin precipitates, but the solubility is 10 mg/mL or less, indicating low solubility of IgM. There is no description at all regarding the stabilization of water-soluble aggregates.

Pharmaceutical Research 1994, 11(5), 624-632 (Non-Patent Document 6) discloses stabilization of IgM by PVP addition, but does not disclose the stabilization of highly concentrated antibodies. Journal of Immunological Methods 1995, 181(1), 37-43 (Non-Patent Document 7) discloses lyophilized formulations produced by addition of trehalose, but in this report, the antibody stability is insufficient and there is no description relating to stabilization of highly concentrated antibodies.

Patent Document 1: WO 2002/096457
Non-Patent Document 1: Proc. Natl. Acad. Sci. U.S.A, (1984) 81:6851
Non-Patent Document 2: Nature (1986) 321:521
Non-Patent Document 3: Clin. Chem. Lab. Med. 2000; 38 (8):759-764
Non-Patent Document 4: BIOTECHNOLOGY 1993, 11, 512-515
Non-Patent Document 5: Journal of Immunological Methods, 111 (1988), 17-23
Non-Patent Document 6: Pharmaceutical Research 1994, 11(5), 624-632
Non-Patent Document 7: Journal of Immunological Methods 1995, 181, 37-43
Non-Patent Document 8: Cytotherapy, 2001, 3(3), 233-242

DISCLOSURE OF THE INVENTION

Problems to be Solved by the Invention

The present invention was achieved in view of the above circumstances. An objective of the present invention is to stabilize highly concentrated IgM in solutions. More specifically, the present invention aims to provide methods for stabilizing highly concentrated IgM, solutions in which highly concentrated IgM is stabilized, and methods for preparing the solutions.

In a preferred embodiment of solutions in which highly concentrated IgM is stabilized, the present invention provides an aqueous solution in which increase of water-soluble aggregates is suppressed. Another preferred embodiment provides a highly concentrated IgM formulation that is stable enough to be used as a pharmaceutical.

Means to Solve the Problems

As a result of dedicated research to solve the above-mentioned problems, the present inventors discovered that, by using compounds comprising polyvalent cationic ions such as magnesium chloride and arginine hydrochloride as additives, aggregation of IgM in solutions may be suppressed and stable highly concentrated IgM solutions may be prepared.

Specifically, the present invention relates to methods for stabilizing highly concentrated IgM, solutions in which highly concentrated IgM is stabilized, and methods for preparing the solutions. More specifically, the present invention provides the following:

(1) a solution wherein a high concentration of immunoglobulin is stabilized, and wherein the immunoglobulin is IgM;
(2) the solution of (1), comprising IgM at a concentration higher than 1 mg/mL;
(3) the solution of (1), which is an aqueous solution;
(4) the solution of (1), which is a pharmaceutical formulation;
(5) the solution of (1), comprising a polyvalent cationic ion;
(6) the solution of (5), comprising the polyvalent cationic ion at a concentration of 1 mM to 1,000 mM;
(7) the solution of (5), wherein the polyvalent cationic ion is a Mg ion or an Arg ion;
(8) the solution of (5), further comprising sugars;
(9) the solution of (1), which is pH 5 to pH 8;
(10) the solution of (1), wherein the solution does not intrinsically comprise human-derived proteins other than IgM;
(11) the solution of (1), wherein the solution does not intrinsically comprise proteins other than IgM;
(12) a pharmaceutical formulation obtained by freezing or lyophilizing the solution of any one of (1) to (11);
(13) a method for stabilizing a solution comprising a high concentration of immunoglobulin, wherein the immunoglobulin is IgM and wherein the method comprises adding a polyvalent cationic ion to the solution;
(14) the method of (13), wherein the solution comprises IgM at a concentration higher than 1 mg/mL;
(15) the method of (13), wherein the solution is an aqueous solution;
(16) the method of (13), wherein the solution is a pharmaceutical formulation;
(17) the method of (13), which comprises adding a polyvalent cationic ion to the solution such that the solution comprises the polyvalent cationic ion at a concentration of 1 mM to 1,000 mM;
(18) the method of (13), wherein the polyvalent cationic ion is a Mg ion or an Arg ion;
(19) the method of (13), further comprising addition of sugars;
(20) the method of (13), wherein the pH of the solution is 5 to 8;
(21) the method of (13), wherein the solution does not intrinsically comprise human-derived proteins other than IgM;
(22) the method of (13), wherein the solution does not intrinsically comprise proteins other than IgM;
(23) a method for stabilizing a pharmaceutical formulation, which comprises the steps of:
 (a) performing the method of any one of (13) to (22); and
 (b) freezing or lyophilizing the solution stabilized in step (a);
(24) a method for producing a solution comprising a high concentration of stabilized immunoglobulin, wherein the immunoglobulin is IgM and wherein the method comprises the step of adding a polyvalent cationic ion to the solution;
(25) the method of (24), wherein the solution comprises IgM at a concentration higher than 1 mg/mL;
(26) the method of (24), wherein the solution is an aqueous solution;
(27) the method of (24), wherein the solution is a pharmaceutical formulation;
(28) the method of (24), which comprises the step of adding a polyvalent cationic ion to the solution such that the solution comprises the polyvalent cationic ion at a concentration of 1 mM to 1000 mM;

(29) the method of (24), wherein the polyvalent cationic ion is a Mg ion or an Arg ion;
(30) the method of (24), which further comprises the step of adding sugars;
(31) the method of (24), wherein the pH of the solution is 5 to 8;
(32) the method of (24), wherein the solution essentially does not comprise human-derived proteins other than IgM;
(33) the method of (24), wherein the solution essentially does not comprise proteins other than IgM;
(34) a solution which is produced by the method of any one of (24) to (33); and
(35) a method for producing a pharmaceutical formulation, wherein the method comprises the steps of:
 (a) performing the method of any one of (24) to (33); and
 (b) freezing or lyophilizing the solution produced in step (a).

DETAILED DESCRIPTION

Figure 1:
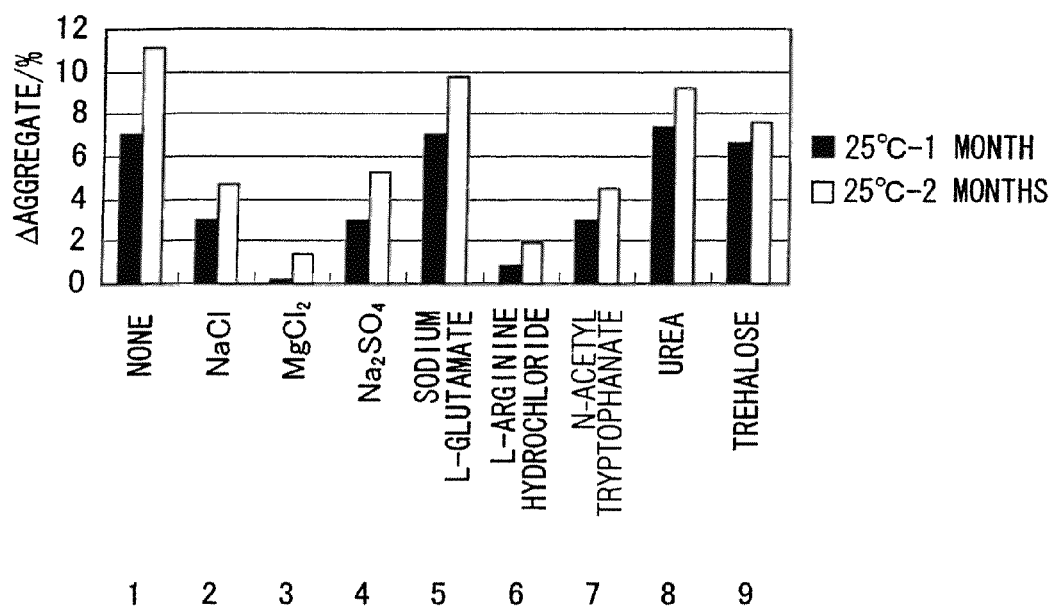
FIG. 1 shows "Δaggregate" values obtained by subtracting the initial aggregate content from the aggregate content after one month of storage at 25° C. (25° C.−1 month) and the aggregate content after 2 months of storage at 25° C. (25° C.−2 months) for each sample.

In the present invention, the term "IgM" refers to an immunoglobulin that comprises constant regions of the μ chain as the constant regions of the heavy chains, and forms a pentameric or hexameric structure. The origin of the variable regions constituting the IgM of the present invention is not limited. Therefore, in addition to a variable region derived from the μ chain, the IgM of the present invention may comprise a variable region derived from IgG, or a partial structure thereof. The partial structure of a variable region can comprise the framework and CDR. The "IgM" in the present invention refers to expression products of exogenous IgM genes introduced into cells for transformation.

Furthermore, the constant regions constituting the IgM of the present invention may be derived from any animal species. That is, the IgM of the present invention comprises an IgM constant region derived from any type of animal species carrying an IgM-type immunoglobulin. When IgM is administered in vivo, at least its constant regions are preferably derived from an animal species same as the species to which the IgM is administered. Therefore, when the IgM is administered to humans, at least its constant regions are preferably derived from humans. IgM composed of constant regions derived from humans, and variable regions derived from another animal species or another human, is called a chimeric antibody. A more preferable IgM for administration to humans is an IgM whose variable region framework is derived from humans, in addition to the constant regions. Human antibodies which have retained the variable region framework structure, but only the CDR has been replaced with that of an antibody from another animal species are called humanized antibodies.

In the present invention, the phrase "highly concentrated immunoglobulin (IgM)" means that the IgM content in a solution is higher than 1 mg/mL. Solutions of the present invention preferably have an IgM content of 1 mg/mL to 200 mg/mL. According to the present invention, IgM can be stabilized even at concentrations higher than 10 mg/mL (for example, 20 mg/mL or more, 25 mg/mL or more, 40 mg/mL or more, or 50 mg/mL or more).

In the present invention, when suppressing an increase of water-soluble aggregates, it is preferable to add a polyvalent cationic ion. A "polyvalent cationic ion" that may be used in the present invention is a divalent or higher valence cationic ion. For example, $Mg^{++}$, $Ca^{++}$, $Zn^{++}$, $Fe^{++}$, or a basic amino acid can be used. As basic amino acids, arginine, lysine, L-lysine L-glutamate, L-arginine L-glutamate, and such may be used. Preferably, the polyvalent cationic ion is $Mg^{++}$ or arginine. In addition to polyvalent cationic ions, cationic ions that may be used in the present invention are monovalent cationic ions, examples being $Na^+$ and $K^+$.

The concentration of cationic ions or polyvalent cationic ions added to solutions is usually 1 mM to 1,000 mM, preferably 10 mM to 500 mM, and more preferably 50 mM to 200 mM.

Solutions of the present invention may comprise sugars in addition to cationic ions or polyvalent cationic ions. Preferred sugars include trehalose, sucrose, and sorbitol.

Types of buffers that may be used in the present invention include phosphate buffers, acetate buffers, and citrate buffers.

The term "stabilization" in the present invention refers to suppressing the increase of water-soluble IgM aggregates produced during storage, and/or suppressing the increase of insoluble IgM aggregates (precipitates) produced during storage, and/or maintaining the function of water-soluble IgM. Preferably, "stabilization" refers to suppressing the increase of water-soluble IgM aggregates produced during storage.

The term "water-soluble aggregates" in the present invention refers to water-soluble multimers such as dimers or trimers of IgM. The water-soluble aggregates can be detected, for example, by gel filtration chromatography. Stabilization of highly concentrated IgM solutions can be measured, for example, from the aggregate increase suppression rate, which can be calculated by using the following formula:

Suppression ratio of aggregate increase=$(A-B)/A \times 100$

A: Percent increase in aggregates in highly concentrated IgM solution without polyvalent cationic ion (control)
B: Percent increase in aggregates in highly concentrated IgM solution with polyvalent cationic ion (test sample)

The aggregate increase suppression rate for the solutions of the present invention one month after addition of polyvalent cationic ions to the solution comprising a high concentration of IgM is preferably 10% or more, more preferably 30% or more, even more preferably 50% or more, and yet even more preferably 80% or more.

Solutions of the present invention are preferably those not comprising human-derived proteins other than IgM. More preferable are solutions not comprising proteins other than IgM in amounts that may make the proteins effective as stabilizers, or in amounts greater than that. When the solutions of the present invention are pharmaceutical formulations, solutions not comprising human-derived proteins other than IgM, in amounts acceptable for a pharmaceutical and/or for a bulk drug substance of a pharmaceutical are preferable, or amounts greater than that.

The dosage form of pharmaceutical formulations of the present invention is not particularly limited, and any discretionary dosage form is possible. Examples of the dosage form include a solution formulation and a lyophilized formulation. Examples of the solution formulations include formulations stored in a cold place, formulations stored at room temperature, and frozen formulations. There are no particular limitations on the administration route for the pharmaceutical formulations of the present invention; any administration route can be used. The pharmaceutical formulations may thus be administered either orally or parenterally depending on the purpose of use.

Specific dosage forms for parenteral administration include injections, and dosage forms for nasal administration, pulmonary administration, and transdermal administration. Systemic or local injections can be carried out by intravenous injections, intramuscular injections, peritoneal injections, subcutaneous injections, or such.

In addition to administering directly to patients as is, IgM stabilized by methods of the present invention can be administered as pharmaceutical agents formulated by well-known pharmaceutical methods. For example, the stabilized IgM can be used as sterile solutions prepared with water or other pharmaceutically acceptable liquid, or as injections of suspensions. Furthermore, it may be formulated by, for example, appropriately combining with pharmaceutically acceptable carriers or media, such as sterilized water, saline, emulsifiers, suspending agents, surfactants, stabilizers, vehicles, and preservatives, and mixing them at a unit dosage form required for generally accepted pharmaceutical practice. The amount of active ingredient in these formulations can be adjusted so that an appropriate dose within an indicated range can be acquired.

Sterile compositions for injections can be formulated according to usual pharmaceutical practice using vehicles such as distilled water for injections. Examples of aqueous solutions used for injections include physiological saline and isotonic solutions comprising glucose and other auxiliary agents. Specifically, the auxiliary agents may be sucrose, D-sorbitol, D-mannose, D-mannitol, sodium chloride, and such. Suitable solubilizers may also be added to pharmaceutical compositions. For example, alcohols and non-ionic surfactants are preferred solubilizers. Specific examples of alcohols comprise ethanol, polyalcohols such as propylene glycol and polyethylene glycol. Examples of non-ionic surfactants may be Polysorbate80, Polysorbate20, Poloxamer188, HCO-50, and such. Cationic surfactants such as benzalkonium chloride may also be used.

Oily fluids may be, for example, sesame oil and soybean oil, and may be used together with benzyl benzoate or benzyl alcohol as a solubilizer. Furthermore, buffers such as phosphate buffer and sodium acetate buffer, analgesic agents such as procain hydrochloride, stabilizers such as benzyl alcohol and phenol, and antioxidants may be combined. The prepared injections are usually loaded into suitable vials or ampules.

When the solutions of the present invention are made into pharmaceutical formulations, their pH is preferably 5 to 8, and particularly preferably 5 to 7.

The administration dose of the pharmaceutical formulations can be appropriately selected according to the disease to be treated, and age and symptoms of the patient. For example, a single dose can be selected within the range of 0.0001 mg to 1,000 mg per 1 kg body weight. Alternatively, for example, the dose can be selected within the range of 0.001 to 100,000 mg/body of patient. However, doses of the pharmaceutical formulations of the present invention are not limited to these. One can refer to WO 2002/096457 for the preparation of liquid formulations and such of the present invention.

All prior art literature cited herein are incorporated herein by reference.

EXAMPLES

Hereinafter, the present invention is specifically illustrated with reference to Examples, but it is not to be construed as being limited thereto.

Example 1

In the following Examples, recombinant anti-ganglioside GM3 human antibody produced in Reference Example 1 (hereinafter, referred to as "MABON-01") was used as the IgM. The MABON-01 solution was concentrated to prepare a highly concentrated solution of approximately 9 mg/mL. For buffer replacement, this solution was dialyzed against buffers 1 to 6 as listed below using a dialysis membrane, SLIDE-A-LYZER Dialysis Cassette 10000MWCO (PIERCE).

1. 20 mM sodium acetate, 300 mM NaCl, pH 5.0/acetate pH 5.0
2. 20 mM sodium acetate, 300 mM NaCl, pH 5.5/acetate pH 5.5
3. 20 mM sodium acetate, 300 mM NaCl, pH 6.0/acetate pH 6.0
4. 20 mM sodium citrate, 300 mM NaCl, pH 5.0/citrate pH 5.0
5. 20 mM sodium citrate, 300 mM NaCl, pH 5.5/citrate pH 5.5
6. 20 mM sodium citrate, 300 mM NaCl, pH 6.0/citrate pH 6.0

The resulting solutions were collected, and the concentration of MABON-01 in each sample was adjusted to 8.4 mg/mL. Each sample was placed in a storage container, Multiply-Safecup 0.1 ml Biosph. (SARSTEDT). Stability tests were carried out on these samples at 4° C. The samples were evaluated at the initial state and after storing at 4° C. for 2 months (hereafter referred to as, for example "4° C.–2 months"). The stability of each sample was evaluated based on changes in the residual monomer ratio determined by gel filtration chromatography. G4000SW$_{XL}$ (TOSOH) was used as the column for gel filtration chromatography. A solution comprising 50 mM sodium phosphate and 500 mM KCl (pH 7.4) was used as the mobile phase. The residual monomer ratio in a sample was calculated from the values of aggregate peak area and monomer peak area obtained as a result of gel filtration chromatography. The residual monomer ratio in each sample at 4° C.–2 months when the residual monomer ratio at the initial state was defined as 100% is summarized in Table 1.

TABLE 1

| | Residual Monomer Ratio (%) | |
|---|---|---|
| pH | Acetate | Citrate |
| 5.0 | 99.33 | 99.16 |
| 5.5 | 99.51 | 99.3 |
| 6.0 | 98.92 | 98.9 |

Thus stable, highly concentrated MABON-01 solutions could be prepared in citrate or acetate buffers (between pH 5.0 and pH 6.0) comprising 300 mM NaCl.

The following Examples describe stabilized and highly concentrated MABON-01 solutions, in which increase of water-soluble aggregates is further suppressed by adding polyvalent cations to solutions comprising citrate buffer (pH 5.5).

Example 2

The MABON-01 solution was concentrated to prepare a highly concentrated solution of approximately 18 mg/mL. This solution was dialyzed using a dialysis membrane, SLIDE-A-LYZER Dialysis Cassette 1000MWCO (PIERCE), to replace the buffer with a solution comprising 20 mM citric acid and 300 mM NaCl (pH 5.5) (the buffer type and pH were optimized under conditions without additives). This highly concentrated MABON-01 solution was dialyzed against the following buffers 1 to 9 using EasySep (TOMY) to replace the buffer.
1. 20 mM sodium citrate, 300 mM NaCl, pH 5.5/no additives
2. 20 mM sodium citrate, 900 mM NaCl, pH 5.5/NaCl
3. 20 mM sodium citrate, 300 mM NaCl, 200 mM $MgCl_2$, pH 5.5/$MgCl_2$
4. 20 mM sodium citrate, 300 mM NaCl, 200 mM $Na_2SO_4$, pH 5.5/$Na_2SO_4$
5. 20 mM sodium citrate, 300 mM NaCl, 100 mM sodium L-glutamate, pH 5.5/sodium L-glutamate
6. 20 mM sodium citrate, 300 mM NaCl, 100 mM L-arginine hydrochloride, pH 5.5/L-arginine hydrochloride
7. 20 mM sodium citrate, 300 mM NaCl, 100 mM sodium N-acetyltryptophanate, pH 5.5/sodium N-acetyltryptophanate
8. 20 mM sodium citrate, 300 mM NaCl, 10 mM urea, pH 5.5/urea
9. 20 mM sodium citrate, 300 mM NaCl, 100 mM trehalose, pH 5.5/trehalose The resulting solutions were collected, and the concentration of MABON-01 in each sample was adjusted to 18.5 mg/mL. Each sample was placed in a storage container, Multiply-Safecup 0.1 ml Biosph. (SARSTEDT). Stability tests were carried out on these samples at 25° C. The samples were evaluated at the initial state, at 25° C.-1 month, and at 25° C.-2 months. The stability of each sample was evaluated based on changes (increase) in aggregate content determined by gel filtration chromatography. $G4000SW_{XL}$ (TOSOH) was used as the column for gel filtration chromatography. A solution comprising 50 mM sodium phosphate and 500 mM KCl (pH 7.4) was used as the mobile phase. The aggregate content in the samples was calculated from the values of aggregate peak area and monomer peak area obtained from gel filtration chromatography. Values obtained by subtracting the aggregate content in the initial state from the aggregate content at 25° C.-1 month and at 25° C.-2 months for each sample are shown in FIG. 1 as Δaggregate values.

As a result, increase of aggregates was suppressed in sample 2 [NaCl (comprising 900 mM NaCl)], when compared to sample 1 [no additives (comprising 300 mM NaCl)]. This showed that increase of aggregates can be suppressed by increasing the NaCl concentration.

Meanwhile, although samples 2 [NaCl (comprising 900 mM NaCl)], 3 [$MgCl_2$ (comprising 300 mM NaCl+200 mM $MgCl_2$)], and 4 [$Na_2SO_4$ (comprising 300 mM NaCl+200 mM $Na_2SO_4$)] all have the same ionic strength (each has an ionic strength of 0.9 M), $MgCl_2$ comprising a divalent cation showed a significant stabilization effect, while sample 4 [$Na_2SO_4$] comprising a divalent anion showed a stabilization effect similar in magnitude to that in sample 2 [NaCl].

Although sample 5 (sodium L-glutamate) and sample 6 (L-arginine hydrochloride) both comprise ionic amino acids, sample 5 comprising sodium L-glutamate did not show a stabilization effect, whereas sample 6 comprising L-arginine hydrochloride, which comprises a divalent cation, showed a stabilization effect similar to that of sample 3 ($MgCl_2$).

The results revealed that increasing the ionic strength by adding salts such as NaCl leads to aggregate suppression. Moreover, at the same ionic strength, use of divalent cations such as magnesium or arginine leads to stronger aggregate suppression effect. However, a strong aggregate suppression effect cannot be obtained by using divalent anions such as sulfate ion and glutamate. More specifically, interaction of a divalent cation such as magnesium ion or arginine with MABON-01 significantly suppressed the aggregation of MABON-01, enabling the preparation of stable and highly concentrated solutions.

Example 3

MABON-01 solution was concentrated to prepare a highly concentrated MABON-01 solution of approximately 19 mg/mL. The solution was dialyzed against the following buffers 1 to 9 using a dialyzer membrane, EasySep® (TOMY), to replace the buffer.
1. 20 mM sodium citrate, 300 mM NaCl, pH5.5
2. 20 mM sodium citrate, 300 mM NaCl, 10 mM $MgCl_2$, pH5.5
3. 20 mM sodium citrate, 300 mM NaCl, 50 mM $MgCl_2$, pH5.5
4. 20 mM sodium citrate, 300 mM NaCl, 200 mM $MgCl_2$, pH5.5
5. 20 mM sodium citrate, 300 mM NaCl, 200 mM $MgCl_2$, 100 mM trehalose, pH5.5
6. 20 mM sodium citrate, 300 mM NaCl, 10 mM L-arginine hydrochloride, pH5.5
7. 20 mM sodium citrate, 300 mM NaCl, 50 mM L-arginine hydrochloride, pH5.5
8. 20 mM sodium citrate, 300 mM NaCl, 100 mM L-arginine hydrochloride, pH5.5
9. 20 mM sodium citrate, 300 mM NaCl, 100 mM L-arginine hydrochloride, 100 mM trehalose, pH5.5

Figure 2:
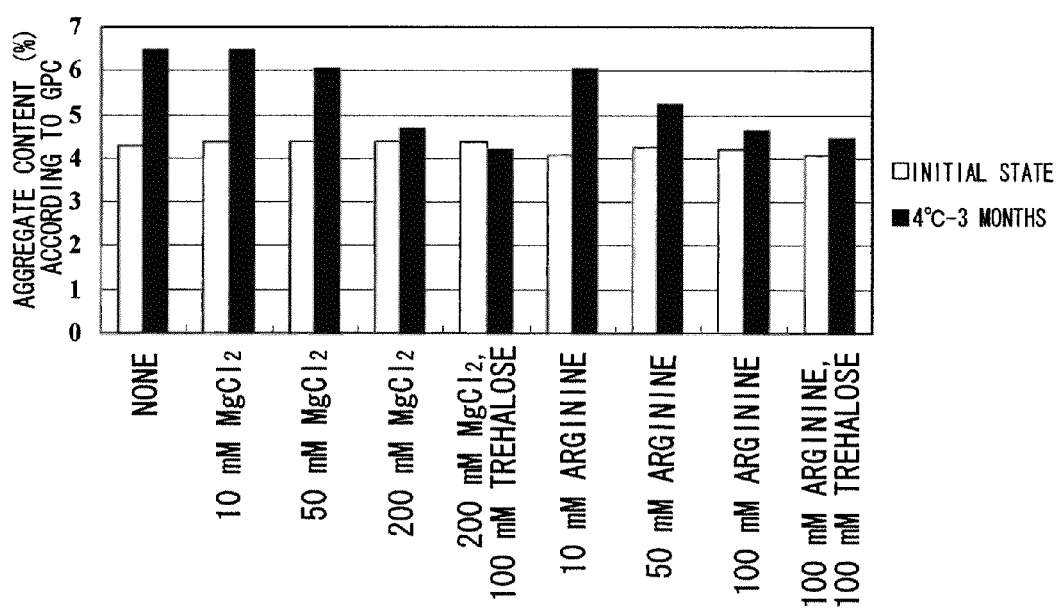
FIG. 2 shows the aggregate content (%) in each sample in the initial state and at 4° C.−3 months.

The resulting solutions were collected, and the concentration of MABON-01 in each sample was adjusted to 18.9 mg/mL. Each sample was placed in a storage container, Multiply-Safecup 0.1 ml Biosph. (SARSTEDT). Stability tests were carried out on these samples. The samples were evaluated at the initial state and at 4° C.-3 months. The stability of each sample was evaluated based on changes (increases) in aggregate content determined by gel filtration chromatography. $G4000SW_{XL}$ (TOSOH) was used as the column for gel filtration chromatography. A solution comprising 50 mM sodium phosphate and 500 mM KCl (pH 7.4) was used as the mobile phase. The aggregate content in the samples was calculated from the values of the aggregate peak area and the monomer peak area obtained from gel filtration chromatography. The aggregate content of each sample at the initial state and at 4° C.-3 months are shown in FIG. 2.

As a result, a $MgCl_2$ and L-arginine hydrochloride concentration-dependent aggregate suppression effect was observed. More specifically, a significant stabilization effect could be obtained by increasing $MgCl_2$ and L-arginine hydrochloride concentrations. Furthermore, while trehalose alone was not effective (Examples 2 and 4), addition of 100 mM trehalose in the presence of 200 mM $MgCl_2$ or 100 mM L-arginine hydrochloride was effective for stabilization.

Example 4

Figure 3:
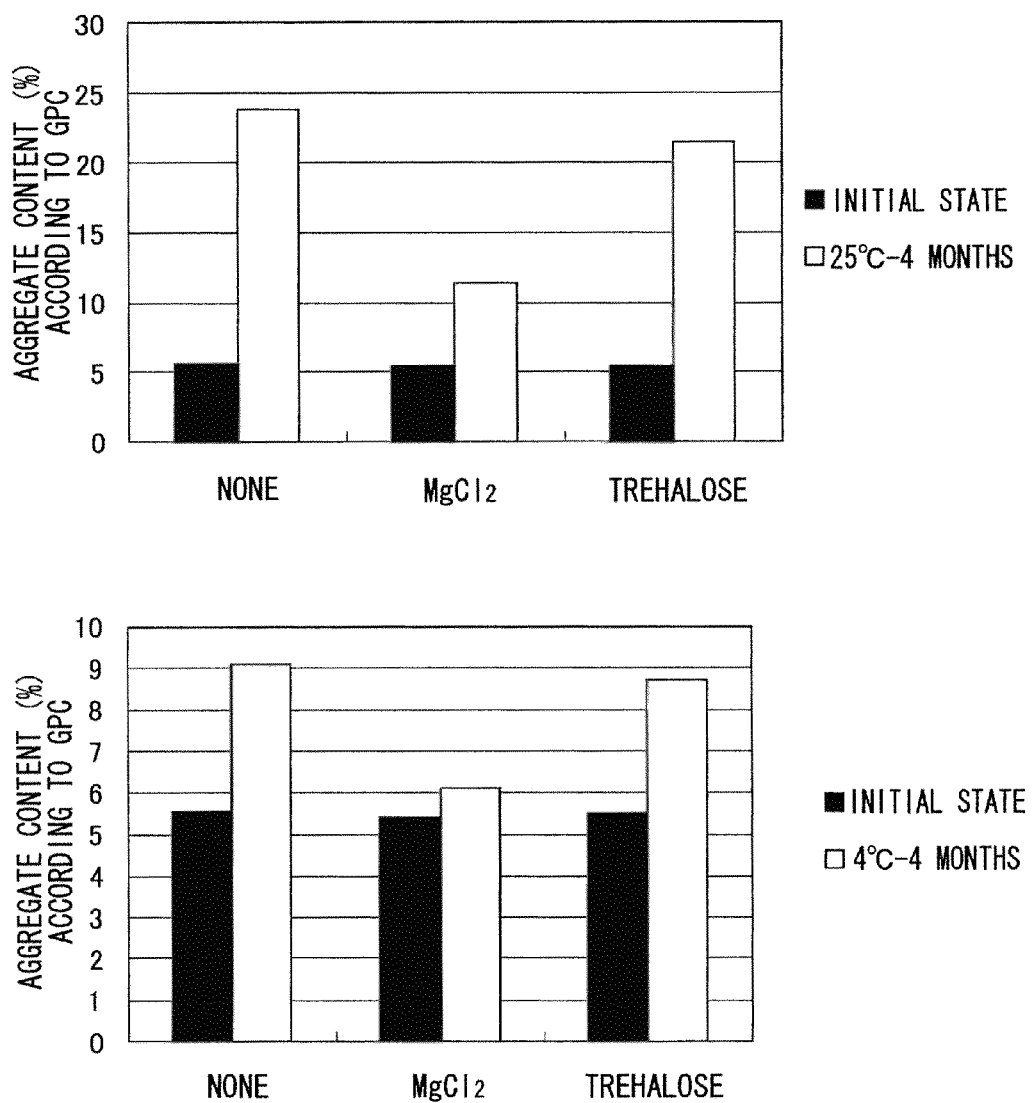
FIG. 3 shows the aggregate content (%) in each sample in the initial state, at 4° C.−4 months, and 25° C.−4 months.

The MABON-01 solution was concentrated to prepare a highly concentrated MABON-01 solution of approximately 27 mg/mL. The solution was dialyzed against the following buffers 1 to 3 using a dialyzer membrane, EasySep® (TOMY), to replace the buffer.
1. 20 mM sodium citrate, 300 mM NaCl, pH5.5/no additives
2. 20 mM sodium citrate, 300 mM NaCl, 200 mM $MgCl_2$, pH5.5/$MgCl_2$
3. 20 mM sodium citrate, 300 mM NaCl, 100 mM trehalose, pH5.5/trehalose The resulting solutions were collected, and the concentration of MABON-01 in each sample was adjusted to 26.8 mg/mL. Each sample was placed in a storage container, Multiply-Safecup 0.1 ml Biosph. (SARSTEDT). Stability tests were carried out on these samples. The samples were evaluated at the initial state, at 4° C.-4 months, and at 25° C.-4 months. The stability of each sample was evaluated based on changes (increases) in aggregate content determined by gel filtration chromatography. G4000SW$_{XL}$ (TOSOH) was used as the column for gel filtration chromatography. A solution comprising 50 mM sodium phosphate and 500 mM KCl (pH 7.4) was used as the mobile phase. The aggregate content in the samples was calculated from the values of aggregate peak area and monomer peak area obtained from gel filtration chromatography. The aggregate content of each sample at the initial state, at 4° C.-4 months, and at 25° C.-4 months are shown in FIG. 3.

As a result, at both 4° C. and 25° C., $MgCl_2$ was observed to have a stabilization effect. On the other hand, such an effect was hardly observed for trehalose, which is known to be a conventional protein stabilizer and which has been found to have a stabilization effect on IgM during lyophilizing as reported in Journal of Immunological Methods 1995, 181(1), 37-43 (FIG. 3).

Example 5

Preparation

A large-scale dialysis of MABON-01 was carried out in "50 mM sodium citrate, 180 mM NaCl, pH5.5, 5% sucrose" buffer, "50 mM sodium citrate, 180 mM ArgHCl, pH5.5, 5% sucrose" buffer, or "50 mM sodium citrate, 180 mM $MgCl_2$, pH5.5, 5% sucrose" buffer. After dialysis, the solutions were concentrated by filter centrifugation. Centrifugation was carried out using VIVASPIN®6 5000MWCO (VIVASCIENCE, VS061) on himac CF8DL (Hitachi, No. SZGEQ054) at 3,000 rpm. After concentrating and collecting the samples, their concentrations were determined based on UV absorption ($\epsilon$=1.40). Next, the samples were diluted to 48.4 mg/mL using the buffers. 1% polysorbate80 solution was further added to each sample to prepare a 0.01% polysorbate formulation. 500 μL each of these samples was individually seeded into 5-mL glass vials, and 30 μL of each sample was placed in Multiply-Safecup 0.1 mL Biosph. (SARSTEDT). The 5-mL glass vials were lyophilized under the following conditions. 1 mg/mL MABON-01 was used as the initial sample, and was stored at 4° C. until analysis.

TABLE 2

| Temperature [° C.] | Time [hr] |
| --- | --- |
| −50 | 24 |
| −20 | 0.02 |
| −20 | 18 |
| 23 | 2.5 |
| 23 | 28 |
| 30 | 0.25 |
| 30 | 10 |
| Total | 82.77 |

Figure 4:
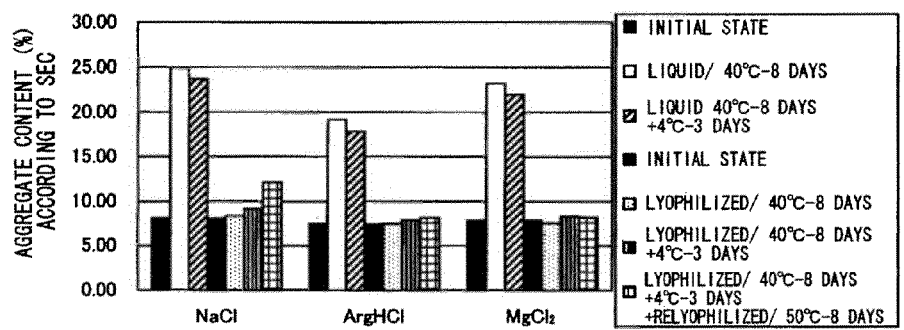
FIG. 4 shows the aggregate content (%) according to size exclusion chromatography (SEC) in each sample in the initial state, liquid/40° C.−8 days, liquid/40° C.−8 days+4° C.−3 days, lyophilized/40° C.−8 days, lyophilized/40° C.−8 days+4° C.−3 days, and lyophilized/40° C.−8 days+4° C.−3 days+relyophilized/50° C.−8 days.

<Experimental Conditions>
"50 mM sodium citrate, 180 mM NaCl, pH 5.5, 5% sucrose, 0.01% polysorbate 80"
"50 mM sodium citrate, 180 mM ArgHCl, pH 5.5, 5% sucrose, 0.01% polysorbate 80"
"50 mM sodium citrate, 180 mM $MgCl_2$, pH 5.5, 5% sucrose, 0.01% polysorbate 80"
MABON-01: 48.4 mg/mL
Liquid/40° C.-8 days
Liquid/40° C.-8 days+4° C.-3 days
Lyophilized/40° C.-8 days
Lyophilized/40° C.-8 days+4° C.-3 days (after reconstitution)
Lyophilized/40° C.-8 days+4° C.-3 days (after reconstitution)+relyophilized/50° C.-8 days
<Analysis>
After incubation, 10 μL of solutions diluted to approximately 1 mg/mL (1/50 dilution solution: 4+296 μL) was analyzed by SEC. "50 mM sodium citrate, 500 mM KCl, pH 7.4" was used as the mobile phase (flow rate: 0.3 mL/min; detection at 280 nm or 220 nm) and SEC analysis was carried out using G4000SW$_{XL}$ (TOSOH) (FIG. 4).

Stability of the lyophilized material was higher with ArgHCl or $MgCl_2$ than with NaCl at the same concentration, even during incubation at 50° C.

Example 6

Preparation

A large-scale dialysis of MABON-01 was carried out using "50 mM sodium citrate, 180 mM NaCl, pH5.5, 5% sucrose" and "50 mM sodium citrate, 180 mM ArgHCl, pH5.5, 5% sucrose" buffers. After dialysis, the solutions were concentrated by filter centrifugation. Centrifugation was carried out using VIVASPIN®6 5000MWCO (VIVASCIENCE, VS061) on himac CF8DL (Hitachi, No. SZGEQ054) at 3,000 rpm. After concentrating and collecting the samples, their concentrations were determined based on UV absorption ($\epsilon$=1.40). 1% polysorbate80 solution was further added to each sample to prepare a 0.01% polysorbate formulation. The samples were diluted to obtain 50 mg/mL formulations. 300 μL each of these samples was individually seeded into three 5-mL glass vials. The 5-mL glass vials were lyophilized under the following conditions. The lyophilized formulations were stored as the initial samples at 4° C. until analysis.

TABLE 3

| Temperature [° C.] | Time [hr] |
| --- | --- |
| −50 | 24 |
| −20 | 0.02 |
| −20 | 18 |
| 23 | 2.5 |

TABLE 3-continued

| Temperature [° C.] | Time [hr] |
|---|---|
| 23 | 28 |
| 30 | 0.25 |
| 30 | 10 |
| Total | 82.77 |

Figure 5:
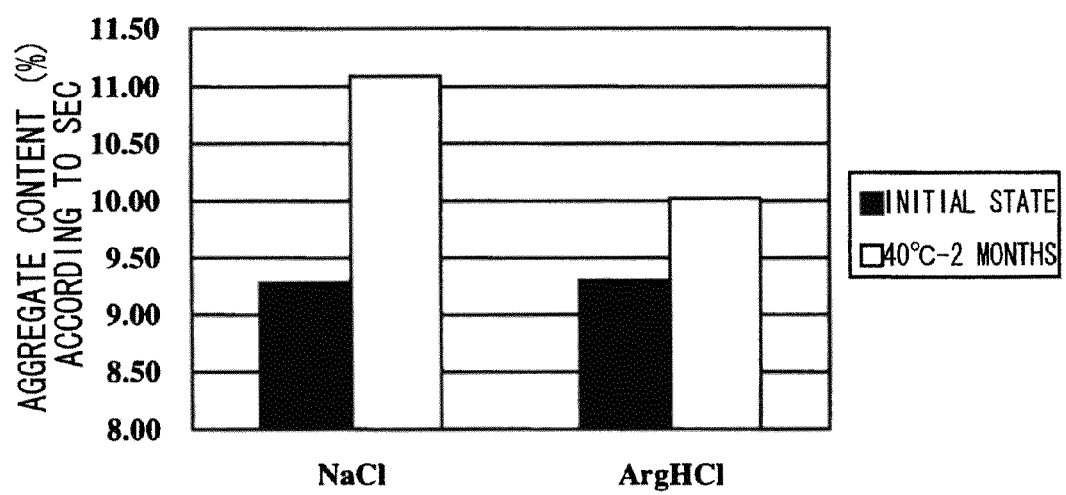
FIG. 5 shows the aggregate content (%) according to SEC in each sample in the initial state, and lyophilized/40° C.−2 months.

<Experimental Conditions>
"50 mM sodium citrate, 180 mM NaCl, pH 5.5, 5% sucrose, 0.01% polysorbate 80"
"50 mM sodium citrate, 180 mM ArgHCl, pH 5.5, 5% sucrose, 0.01% polysorbate 80"
MABON-01: 50 mg/mL
Lyophilized/40° C.−2 months
<Analysis>
After incubation, 10 µL of solutions diluted to approximately 1 mg/mL (1/50 dilution solution: 4+296 µL) was analyzed by SEC. The sample obtained by using "50 mM sodium citrate, 500 mM KCl, pH 7.4" was used as the mobile phase (0.3 mL/min of flow rate; detection at 280 nm or 220 nm) and SEC analysis was carried out using G4000SW$_{XL}$ (TOSOH) (FIG. 5).

Stabilization effect was higher with ArgHCl than with NaCl at the same concentration, even after a long-term accelerated study at 40° C.−2 months.

Reference Example 1

Production of Recombinant Human Antibodies against Ganglioside GM3

1.1 Construction of Anti-Ganglioside GM3 Human Antibody Heavy Chain Gene

A gene encoding the heavy chain of a human antibody that binds to ganglioside GM3 was amplified by RT-PCR using total RNAs extracted from human B cells transformed with Epstein-Barr virus (hereinafter, denoted as anti-ganglioside GM3 human antibody-expressing B cells).

Total RNAs were extracted from $1 \times 10^7$ anti-ganglioside GM3 human antibody-expressing B cells using RNeasy Plant Mini Kit (QIAGEN). Two oligonucleotides (LMH-f3 and LMH-r3) were designed based on the nucleotide sequence of anti-ganglioside GM3 human antibody gene reported by Hoon et al. (Cancer Research 1993; 53: 5244-5250). LMH-f3 (SEQ ID NO: 7) was synthesized in the sense direction, and LMH-r3 (SEQ ID NO: 8) was synthesized in the antisense direction. Using 1 µg of total RNAs, gene fragments were amplified separately for the 5' end and the 3' end by SMART™ RACE cDNA Amplification Kit (CLONTECH). Synthetic oligonucleotides LMH-r3 and LMH-f3 were used for amplifying the 5' and 3' ends of the gene, respectively. Reverse transcription reaction was carried out at 42° C. for 1.5 hours.
The composition of the PCR reaction solution (50 µL) is shown below:
5 µL of 10× Advantage 2 PCR Buffer,
5 µL of 10× Universal Primer A Mix,
0.2 mM dNTPs (dATP, dGTP, dCTP, and dTTP),
1 µL of Advantage 2 Polymerase Mix,
(All the above were from CLONTECH)
2.5 µL of reverse transcription product, and
10 pmol of synthetic oligonucleotide LMH-f3 or LMH-r3.
The reaction was carried out under the conditions of:
94° C. (initial temperature) for 30 seconds,
5 cycles of 94° C. for 5 seconds and 72° C. for 3 minutes,
5 cycles of 94° C. for 5 seconds, 70° C. for 10 seconds, and 72° C. for 3 minutes,
25 cycles of 94° C. for 5 seconds, 68° C. for 10 seconds, and 72° C. for 3 minutes, and finally 72° C. for 7 minutes.

The PCR products were purified from agarose gel using QIAquick Gel Extraction Kit (QIAGEN), and then cloned into pGEM-T Easy vector (Promega). After sequencing, an approximately 1.1 kbp fragment was obtained by digesting the vector comprising the 5' end of the gene using restriction enzymes ApaI (Takara Shuzo) and SacII (Takara Shuzo), while an approximately 1.1 kbp fragment was obtained by digesting the vector comprising the 3' end of the gene using restriction enzymes ApaI (Takara Shuzo) and NotI (Takara Shuzo). The fragments were then mixed, and cloned into pBluescript KS+ vector (TOYOBO) to obtain a full-length anti-ganglioside GM3 human antibody heavy chain gene.

To clone into vectors for expression in animal cells, full-length gene fragments were amplified using synthetic oligonucleotides LMH-fxho and LMH-rsal. LMH-fxho (SEQ ID NO: 11) is a forward primer designed to hybridize to the 5' end of the anti-ganglioside GM3 human antibody heavy chain gene, and to comprise an XhoI restriction enzyme recognition sequence and a Kozak sequence. LMH-rsal (SEQ ID NO: 12) is a reverse primer designed to hybridize to the 3' end of the anti-ganglioside GM3 human antibody heavy chain gene, and to comprise a SalI restriction enzyme recognition sequence.
The composition of the PCR reaction solution (50 µL) is shown below:
5 µL of 10×PCR Buffer,
1 mM MgSO$_4$,
0.2 mM dNTPs (dATP, dGTP, dCTP, and dTTP),
1 unit of DNA polymerase KOD-Plus,
(All the above were from TOYOBO),
10 ng of pBluescript KS+ vector comprising the full-length anti-ganglioside GM3 human antibody heavy chain gene, and
10 pmol of synthetic oligonucleotides LMH-fxho and LMH-rsal.
The reaction was carried out under conditions of:
94° C. (initial temperature) for 2 minutes,
30 cycles of 94° C. for 15 seconds, 60° C. for 30 seconds, and 68° C. for 2 minutes, and finally 72° C. for 5 minutes.

The amplified gene fragment was cloned by digesting with the XhoI restriction enzyme (Takara Shuzo) and the SalI restriction enzyme (Takara Shuzo), then purifying using QIAquick PCR Purification Kit (QIAGEN), and linking to the XhoI restriction enzyme site of pUCAG. This pUCAG vector is obtained by: linking the 2.6 kbp fragment obtained by digesting pCXN (Niwa et al., Gene 1991; 108: 193-200) using the BamHI restriction enzyme to the BamHI restriction enzyme site of pUC19 vector (TOYOBO). The obtained plasmid was named pUCAG/L612H. The nucleotide sequence and amino acid sequence of the anti-ganglioside GM3 human antibody heavy chain in this plasmid are shown in SEQ ID NOs: 1 and 2, respectively.

1.2 Construction of Anti-Ganglioside GM3 Human Antibody Light Chain Gene

A gene encoding the light chain of anti-ganglioside GM3 human antibody was amplified by RT-PCR using total RNAs extracted from the anti-ganglioside GM3 human antibody-expressing B cells. The total RNAs were extracted from the anti-ganglioside GM3 human antibody-expressing B cells in a manner similar to that mentioned above. Two oligonucleotides (LML-f1 and LML-r1) were designed based on the nucleotide sequence of anti-ganglioside GM3 human antibody gene reported by Hoon et al. (Cancer Research 1993;

53: 5244-5250). LML-f1 (SEQ ID NO: 9) and LML-r1 (SEQ ID NO: 10) were synthesized in the sense and antisense directions, respectively.

Using 1 μg of total RNAs, gene fragments were amplified separately for the 5' end and the 3' end by the SMART™ RACE cDNA Amplification Kit (CLONTECH). Synthetic oligonucleotides LML-r1 and LML-f1 were used for amplifying the 5' and 3' ends of the gene, respectively. Reverse transcription reaction was carried out at 42° C. for 1.5 hours. The composition of the PCR reaction solution (50 μL) is shown below:

5 μL of 10× Advantage 2 PCR Buffer,
5 μL of 10× Universal Primer A Mix,
0.2 mM dNTPs (dATP, dGTP, dCTP, and dTTP),
1 μL of Advantage 2 Polymerase Mix,
(All the above were from CLONTECH)
2.5 μL of reverse transcription product, and
10 pmol of synthetic oligonucleotide LML-f1 or LML-r1
The reaction was carried out under conditions of:
94° C. (initial temperature) for 30 seconds,
5 cycles of 94° C. for 5 seconds and 72° C. for 3 minutes,
5 cycles of 94° C. for 5 seconds, 70° C. for 10 seconds, and 72° C. for 3 minutes,
25 cycles of 94° C. for 5 seconds, 68° C. for 10 seconds, and 72° C. for 3 minutes, and finally 72° C. for 7 minutes.

PCR product was purified from the agarose gel using QIAquick Gel Extraction Kit (QIAGEN), and then cloned into pGEM-T Easy vector (Promega). After sequencing, an approximately 0.7 kbp fragment was obtained by digesting the vector comprising the 5' end of the gene using the EcoRI restriction enzyme (Takara Shuzo), while an approximately 0.9 kbp fragment was obtained by digesting the vector comprising the 3' end of the gene using the EcoRI restriction enzyme (Takara Shuzo). The two fragments were mixed, and used to amplify the full-length gene fragment using synthetic oligonucleotides LML-feco and LML-rnot. LML-feco (SEQ ID NO: 13) is a forward primer, and was designed to hybridize to the 5' end of the anti-ganglioside GM3 human antibody light chain gene, and to comprise an EcoRI restriction enzyme recognition sequence and a Kozak sequence. LML-rnot (SEQ ID NO: 14) is a reverse primer, and was designed to hybridize to the 3' end of the anti-ganglioside GM3 human antibody light chain gene, and to comprise a NotI restriction enzyme recognition sequence.

The composition of the PCR reaction solution (50 μL) is shown below:
5 μL of 10×PCR Buffer,
1 mM MgSO$_4$,
0.2 mM dNTPs (dATP, dGTP, dCTP, and dTTP),
1 unit of DNA polymerase KOD-Plus,
(All the above were from TOYOBO)
5'-end gene fragment,
3'-end gene fragment, and
10 pmol of synthetic oligonucleotides LML-feco and LML-rnot.
The reaction was carried out under conditions of:
94° C. (initial temperature) for 2 minutes,
30 cycles of 94° C. for 15 seconds, 60° C. for 30 seconds, and 68° C. for 2 minutes, and finally 72° C. for 5 minutes.

The amplified gene fragment was cloned by digesting with the EcoRI restriction enzyme (Takara Shuzo) and the NotI restriction enzyme (Takara Shuzo), then purifying using QIAquick PCR Purification Kit (QIAGEN) and linking to the EcoRI and NotI restriction enzyme cleavage sites of pCXND3.

The pCXND3 vector was constructed as follows: DHFR-ΔE-rvH-PM1-f (see WO 92/19759) was digested at the EcoRI/SmaI restriction enzyme site to separate their antibody heavy chain gene and vector region. Only the vector portion was then collected, into which the EcoRI-NotI-BamHI adaptor (Takara Shuzo) was cloned. This vector was named pCHOI.

A vector in which the DHFR gene expression site of pCHOI is cloned into the HindIII restriction enzyme site of pCXN (Niwa et al., Gene 1991; 108:193-200) was named pCXND3. Furthermore, the light-chain gene fragment was cloned into pCXND3 and the obtained plasmid was named pCXND3/L612L. The nucleotide sequence and amino acid sequence of anti-ganglioside GM3 human antibody light chain in this plasmid are shown in SEQ ID NOs: 3 and 4, respectively.

1.3 Construction of the Anti-Ganglioside GM3 Human Antibody Expression Vector

To produce the anti-ganglioside GM3 human antibody expression vector, pUCAG/L612H was digested with the HindIII restriction enzyme (Takara Shuzo), and the resulting approximately 4.0 kbp fragment was linked to the HindIII restriction enzyme cleavage site of pCXND3/1612L. The obtained plasmid was named pCXND3/L612IgM. This plasmid expresses the neomycin-resistance gene, DHFR gene, and anti-ganglioside GM3 human antibody gene in animal cells.

1.4 Construction of Anti-Ganglioside GM3 Human Antibody J-Chain Gene and Expression Vector A gene encoding the J chain of anti-ganglioside GM3 human antibody was amplified by RT-PCR using total RNAs extracted from anti-ganglioside GM3 human antibody-expressing B cells. Total RNAs were extracted from anti-ganglioside GM3 human antibody-expressing B cells in a manner similar to that mentioned above. Two oligonucleotides (J-f1 and J-r1) were designed and synthesized based on the nucleotide sequence of the human antibody J chain gene registered in GenBank (GenBank accession number: M12759). J-f1 (SEQ ID NO: 15) hybridizes to human antibody J chain gene Exon 3 in the sense direction, and J-r1 (SEQ ID NO: 16) hybridizes to the human antibody J chain gene Exon 4 in the antisense direction.

Using 1 μg of total RNAs, gene fragments were amplified separately for the 5' end and the 3' end by the SMART™ RACE cDNA Amplification Kit (CLONTECH). Synthetic oligonucleotides J-r1 and J-f1 were used for amplifying the 5' and 3' ends of the gene, respectively. Reverse transcription reaction was carried out at 42° C. for 1.5 hours.

The composition of the PCR reaction solution (50 μL) is shown below:
5 μL of 10× Advantage 2 PCR Buffer,
5 μL of 10× Universal Primer A Mix,
0.2 mM dNTPs (DATP, dGTP, dCTP, and dTTP),
1 μL of Advantage 2 Polymerase Mix,
(All the above were all from CLONTECH)
2.5 μL of reverse transcription product, and
10 pmol of synthetic oligonucleotide J-f1 or J-r1
The reaction was carried out under conditions of:
94° C. (initial temperature) for 30 seconds,
5 cycles of 94° C. for 5 seconds and 72° C. for 3 minutes,
5 cycles of 94° C. for 5 seconds, 70° C. for 10 seconds, and 72° C. for 3 minutes,
25 cycles of 94° C. for 5 seconds, 68° C. for 10 seconds, and 72° C. for 3 minutes, and finally 72° C. for 7 minutes.

PCR product was purified from the agarose gel using QIAquick Gel Extraction Kit (QIAGEN), and then cloned into pGEM-T Easy vector (Promega).

After sequencing, an approximately 0.5 kbp fragment was obtained by digesting the vector comprising the 5' end of the gene using the EcoRI restriction enzyme (Takara Shuzo), and an approximately 1.0 kbp fragment was obtained by digesting the vector comprising the 3' end of the gene using the EcoRI restriction enzyme (Takara Shuzo). The two fragments were mixed, and used to amplify the full-length gene fragment using synthetic oligonucleotides J-feco and J-rxba.

J-feco (SEQ ID NO: 17) is a forward primer designed to hybridize to the 5' end of the anti-ganglioside GM3 human antibody J chain gene, and to comprise an EcoRI restriction enzyme recognition sequence and a Kozak sequence. J-rxba (SEQ ID NO: 18) is a reverse primer designed to hybridize to the 3' end of the anti-ganglioside GM3 human antibody J chain gene, and to comprise an XbaI restriction enzyme recognition sequence.

The composition of the PCR reaction solution (50 µL) is shown below:
5 µL of 10×PCR Buffer,
1 mM $MgSO_4$,
0.2 mM dNTPs (dATP, dGTP, dCTP, and dTTP),
1 unit of DNA polymerase KOD-Plus
 (the above-mentioned ingredients were all from TOYOBO),
5'-end gene fragment,
3'-end gene fragment, and
10 pmol of synthetic oligonucleotides LML-feco and LML-rxba The reaction was carried out under conditions of:
94° C. (initial temperature) for 2 minutes,
30 cycles of 94° C. for 15 seconds, 60° C. for 30 seconds, and 68° C. for 2 minutes, and finally 72° C. for 5 minutes.

The amplified gene fragment was cloned by digesting with the EcoRI restriction enzyme (Takara Shuzo) and the XbaI restriction enzyme (Takara Shuzo), then purifying using QIAquick PCR Purification Kit (QIAGEN), and linking to the EcoRI and XbaI restriction enzyme cleavage sites of pCOSII-Zeo.

This pCOSII-Zeo vector is obtained by removing the DHFR gene expression site of pCHOI, and cloning the Zeocin-resistant gene expression site thereto. The obtained plasmid was named pCOSII-Zeo/J chain. The nucleotide sequence and amino acid sequence of anti-ganglioside GM3 human antibody J chain in this plasmid are shown in SEQ ID NOs: 5 and 6, respectively.

1.5 Expression of Anti-Ganglioside GM3 Human Antibody Using Animal Cells

Stable expression cell lines derived from CHO cells (DG44 line) were produced as described below.

Genes were introduced by electroporation using Gene Pulser II (BioRad).

Introduction of genes to obtain cell lines that do not express the J chain is described below. 0.75 mL of CHO cells suspended in PBS ($1 \times 10^7$ cells/mL) was mixed with anti-ganglioside GM3 human antibody expression vector pCXND3/L612IgM (25 µg), cooled on ice for 10 minutes, transferred to a cuvette, and then pulsed at 1.5 kV and 25 µFD.

After a recovery period of 10 minutes at room temperature, the electroporated cells were suspended in 40 mL of CHO-S-SFMII medium (Invitrogen) comprising 1×HT Supplement (Invitrogen). A 50-fold diluted solution was further prepared using the same medium, and then aliquoted at 100 µL/well into a 96-well culture plate. After incubation for 24 hours in a $CO_2$ incubator (5% $CO_2$), Geneticin (Invitrogen) was added to the wells at 0.5 mg/mL and cultured for 2 weeks.

The IgM levels in the culture supernatants of wells in which colonies of Geneticin-resistant transformants were found were measured by the concentration assay described in Reference Example 1.6. Cell lines highly expressing the anti-ganglioside GM3 human antibodies were successively expanded to obtain anti-ganglioside GM3 human antibody-expressing stable cell lines CA02, CA15, CA19, CA20, and CA24.

Introduction of genes to obtain cell lines expressing the J chain is described below. 0.75 mL of CHO cells suspended in PBS ($1 \times 10^7$ cells/mL) was mixed with anti-ganglioside GM3 human antibody expression vector pCXND3/L612IgM (25 µg) and J chain expression vector pCOSII-Zeo/J chain (20 µg), cooled on ice for 10 minutes, transferred to a cuvette, and then pulsed at 1.5 kV and 25 µFD.

After recovered for 10 minutes at room temperature, the electroporated cells were suspended in 40 mL of CHO-S-SFMII medium (Invitrogen) comprising 1×HT Supplement (Invitrogen).

A 50-fold diluted solution was further prepared using the same medium and aliquoted at 100 µL/well into a 96-well culture plate. After incubation for 24 hours in a $CO_2$ incubator (5% $CO_2$), 0.5 mg/mL Geneticin (Invitrogen) and 0.6 mg/mL Zeocin (Invitrogen) were added to wells, and cultured for 2 weeks. The IgM levels in the culture supernatants of wells in which colonies of Geneticin- and Zeocin-resistant transformants were found were measured by the concentration assay described in Reference Example 1.6. Cell lines highly expressing the anti-ganglioside GM3 human antibodies were successively expanded to obtain anti-ganglioside GM3 human antibody-expressing stable cell lines (CJ15, CJ25, CJ38, CJ45, and CJ67).

1.6 Measurement of IgM Concentration in Culture Supernatants

IgM concentration in the culture supernatants was measured as described below. Anti-Human IgM (BIOSOURCE) was diluted using a coating buffer (0.1 M $NaHCO_3$ and 0.02% $NaN_3$) to prepare a 1 µg/mL solution. The diluted solution was added to a 96-well ELISA plate at 100 µL/well, and then reacted at 4° C. for 24 hours or longer to coat the plate.

After washing the wells with Rinse Buffer, blocking was carried out by adding 200 µL/well of Diluent Buffer and reacting at room temperature for 1 hour or longer. Compositions of the Rinse Buffer and Diluent Buffer are shown below.
 Rinse Buffer: PBS(−)
 0.05% Tween20
 Diluent Buffer: 50 mM Tris,
 1 mM $MgCl_2$,
 0.15 M NaCl,
 0.05% Tween20,
 0.02% $NaN_3$,
 1% BSA Next, culture supernatant suitably diluted with Diluent Buffer was added to the wells at 100 µL/well, and allowed to react at room temperature for 1 hour. After washing with Rinse Buffer, alkaline phosphatase-conjugated goat anti-human IgM (BIOSOURCE) diluted 4,000 times with Diluent Buffer was added at 100 µL/well, and reacted at room temperature for 1 hour. Finally, wells were washed with Rinse Buffer, and alkaline phosphatase substrate (SIGMA) was added thereto. The absorbance was determined at the 405 nm measurement wavelength and 655 nm reference wavelength using Benchmark Plus absorption spectrometer (BioRad). The concentration of IgM was calculated by comparing with a purified anti-ganglioside GM3 human antibody (Hoon et al., Cancer Research 1993; 53: 5244-5250).

Each type of stable cell line expressing anti-ganglioside GM3 human antibodies was cultured in a 75 $cm^2$-culture flask at an initial cell density of $2 \times 10^5$ cells/mL. The IgM concentration in the culture supernatants was measured by the method described above. The results are shown in Table 4. The amount of IgM produced was approximately 20 mg/L on the third day and approximately 50 mg/L on the seventh day. The productivity indicating the production ability of a single cell was 5 to 19 pg/cell/day. Since IgM is a type of immunoglobulin that forms multimers, expression level of IgM in recombinants is low, and therefore, its large-scale preparation was considered difficult. However, the present results showed that highly productive recombinant IgM-expressing cells can be produced from CHO cells.

TABLE 4

| J-chain expression | Cell lines | Production amount after culturing for 3 days (mg/L) | Production amount after culturing for 7 days (mg/L) | Productivity (pg/cell/day) |
|---|---|---|---|---|
| Absent | CA02 | 24.1 | 36.9 | 14.1 |
|  | CA15 | 11.8 | 39.7 | 4.9 |
|  | CA19 | 27.1 | 62.3 | 13.1 |
|  | CA20 | 20.2 | 35.4 | 10.5 |
|  | CA24 | 25.0 | 41.5 | 10.7 |
| Present | CJ15 | 29.4 | N.T. | 19.4 |
|  | CJ25 | 24.4 | N.T. | 18.1 |
|  | CJ38 | 14.9 | N.T. | 12.4 |
|  | CJ45 | 26.4 | N.T. | 18.7 |
|  | CJ67 | 18.0 | N.T. | 12.8 |

N.T.: Not Tested

Reference Example 2

Measurement of Aggregates (1)

Gel filtration chromatographic analysis of MABON-01 was carried out using the following buffers as mobile phase. In all analyses, a TSKgel G4000SW$_{XL}$ column was used, the flow rate was 0.3 mL/min, absorbance at 280 nm was detected, and the injection amount of samples was 10 μg.
1. 50 mM sodium phosphate, 500 mM KCl, pH 6.2
2. 50 mM sodium phosphate, 500 mM KCl, pH 6.5
3. 50 mM sodium phosphate, 500 mM KCl, pH 6.8
4. 50 mM sodium phosphate, 500 mM KCl, pH 7.1
5. 50 mM sodium phosphate, 500 mM KCl, pH 7.4
6. 50 mM sodium phosphate, 300 mM KCl, pH 6.5
7. 50 mM sodium phosphate, 300 mM KCl, pH 7.4
8. 50 mM sodium phosphate, 500 mM NaCl, pH 6.5
9. 50 mM sodium phosphate, 500 mM NaCl, pH 7.4
10. 50 mM sodium phosphate, 300 mM NaCl, pH 6.5
11. 50 mM sodium phosphate, 300 mM NaCl, pH 7.4

The aggregate peak area and the monomer peak area values (peak assignments were carried out separately) based on the obtained chromatograms are shown in Table 5.

Table 6 shows the result of calculating the aggregate peak area rate and the monomer peak area rate relative to the total peak area value.

TABLE 6

|  | KCl | | KCl | | NaCl | | NaCl | |
|---|---|---|---|---|---|---|---|---|
|  | 500 mM | | 300 mM | | 500 mM | | 300 mM | |
|  |  |  |  |  |  |  | Aggregate | Monomer |
| pH 6.2 | 4.8 | 95.2 | — | — | — | — | — | — |
| pH 6.5 | 5.0 | 95.0 | 4.2 | 95.8 | 4.2 | 95.8 | 2.9 | 97.1 |
| pH 6.8 | 5.0 | 95.0 | — | — | — | — | — | — |
| pH 7.1 | 5.1 | 94.9 | — | — | — | — | — | — |
| pH 7.4 | 5.3 | 94.7 | 5.1 | 94.9 | 4.6 | 95.4 | 3.8 | 96.2 |

In each cell, the aggregate peak area rates are shown on the left, and the monomer peak area rates are shown on the right.

These results revealed that, for both the total peak area values and the aggregate peak area rates, the effects of salt type and salt concentration are suppressed when a pH 7.4 mobile phase buffer is used, compared to when mobile phase buffers of pH 6.2 to 7.1 are used. In addition, it was revealed that the effect of pH is suppressed when the salt concentration in the mobile phase buffer comprising either KCl or NaCl is 500 mM, compared to when the salt concentration is 300 mM. Furthermore, it was revealed that the effects of salt concentration and mobile phase pH are suppressed when a mobile phase buffer comprises KCl, compared to when a mobile phase buffer comprises NaCl. Therefore, conditions for the mobile phase for the gel filtration chromatographic analysis of MABON-01 were set at 50 mM sodium phosphate, 500 mM KCl, and pH 7.4.

Reference Example 3

Measurement of Aggregates (2)

GPC-MALLS analysis of MABON-01 was carried out to determine the molecular weight of each peak. The mobile phase buffer was 50 mM sodium phosphate, 500 mM KCl, pH 7.4. TSKgel G4000SW$_{XL}$ column was used. The flow rate was 0.3 mL/min. Absorbance at 280 nm was detected. Injection amount of samples was 113 μg. According to the obtained results, the molecular weights were calculated by the Debye method.

Figure 6:
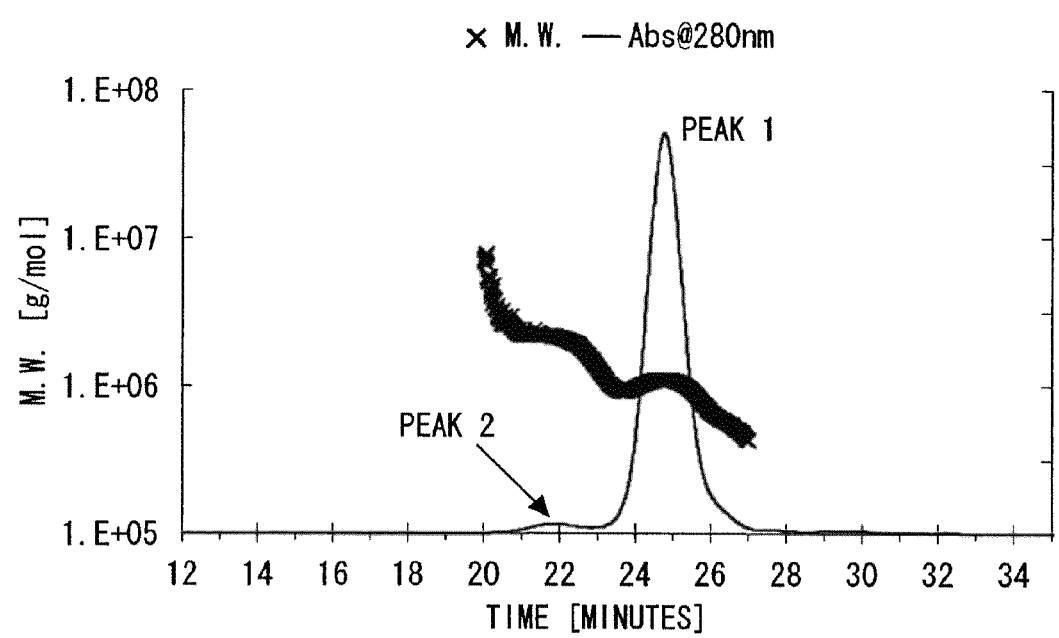
FIG. 6 shows the chromatogram obtained by gel permeation chromatography (GPC)-MALLS analysis of MABON-01 and the molecular weight determined by calculation.

Resulting chromatogram and the calculated molecular weights are shown as a superimposed diagram in FIG. 6. The average molecular weights of peak 1 and peak 2 in the figure, and the theoretical molecular weight of MABON-01 calculated from its amino acid sequence are shown in Table 7.

TABLE 5

|  | KCl | | | | NaCl | | | |
|---|---|---|---|---|---|---|---|---|
|  | 500 mM | | 300 mM | | 500 mM | | 300 mM | |
| pH 6.2 | 3073386 | | — | | — | | Total peak area value | |
|  | 146342 | 2927044 | — | — | — | — | Aggregate | Monomer |
| pH 6.5 | 3096904 | | 2959509 | | 3044989 | | 2818198 | |
|  | 155304 | 2941600 | 124880 | 2834629 | 127467 | 2917522 | 82928 | 2735270 |
| pH 6.8 | 3074760 | | — | | — | | — | |
|  | 153682 | 2921078 | — | — | — | — | — | — |
| pH 7.1 | 3033846 | | — | | — | | — | |
|  | 154085 | 2879761 | — | — | — | — | — | — |
| pH 7.4 | 3074597 | | 3098757 | | 3130093 | | 2948932 | |
|  | 163747 | 2910850 | 157320 | 2941437 | 144630 | 2985463 | 112427 | 2836505 |

In each cell, the total peak area value is shown in the top row, the area value for the aggregate is shown in the bottom row on the left, and the area value for the monomer is shown in the bottom row on the right.

TABLE 7

| Average molecular weights | | Theoretical molecular weights | |
|---|---|---|---|
| | M.W. [kDa] | | M.W. [kDa] |
| Peak 1 | 1,109 | Monomer | 1,034 |
| Peak 2 | 2,193 | Dimer | 2,068 |

The average molecular weights were obtained by averaging the molecular weights corresponding to 21.5 to 22.0 minutes for peak 2, and 24.5 to 25.0 minutes for peak 1. The average molecular weight values for peak 1 and peak 2 are close to the theoretical molecular weight values for the monomer and dimer, respectively. In addition, the average molecular weight value for peak 2 is approximately two times that of peak 1. Accordingly, peak 1 was found to comprise the MABON-01 monomer, and peak 2 was found to comprise the dimer.

INDUSTRIAL APPLICABILITY

The present invention enabled stabilization of highly concentrated IgM in solutions. Since the present invention enables stable long-term storage of pharmaceutical formulations comprising IgM as an active ingredient, it can significantly contribute to particularly the preparation of antibody formulations.

The invention claimed is:

1. An aqueous solution of IgM comprising at least 1 mg/mL IgM, citrate buffer, and a polyvalent cation that is Mg++ or arginine ion, wherein the polyvalent cation is present at a concentration that suppresses by at least 10% the increase of water-soluble IgM aggregates produced during storage of the solution at a temperature selected from 4° C., 25° C., and 40° C., compared to the increase of water-soluble IgM aggregates seen with the same solution without the polyvalent cation.

2. The solution of claim 1, wherein the polyvalent cation is Mg++.

3. The solution of claim 1, wherein the polyvalent cation is arginine ion.

4. The solution of claim 1, wherein the degree of suppression is at least 30%.

5. The solution of claim 1, wherein the degree of suppression is at least 50%.

6. The solution of claim 1, wherein the degree of suppression is at least 80%.

7. The solution of claim 1, wherein the IgM concentration is 1-200 mg/mL.

8. The solution of claim 1, wherein the concentration of IgM in the solution is higher than 10 mg/mL.

9. The solution of claim 1, wherein the concentration of IgM in the solution is 20 mg/mL or more.

10. The solution of claim 1, wherein the concentration of IgM in the solution is 25 mg/mL or more.

11. The solution of claim 1, wherein the concentration of IgM in the solution is 40 mg/mL or more.

12. The solution of claim 1, wherein the concentration of IgM in the solution is 50 mg/mL or more.

13. The solution of claim 1, wherein the concentration of the polyvalent cation in the solution is 1 mM to 1000 mM.

14. The solution of claim 1, wherein the concentration of the polyvalent cation in the solution is 10 mM to 500 mM.

15. The solution of claim 1, wherein the concentration of the polyvalent cation in the solution is 50 mM to 200 mM.

16. The solution of claim 1, wherein the pH of the solution is 5 to 8.

17. The solution of claim 1, wherein the solution does not comprise proteins other than IgM.

18. A method for preparing the solution of claim 1, the method comprising adding the polyvalent cation to a first solution comprising the IgM to form a second solution comprising the IgM at 1 mg/mL or more, citrate buffer, and the polyvalent cation.

19. The method of claim 18, wherein the concentration of the IgM in the second solution is 20 mg/mL or more.

20. The method of claim 18, further comprising storing the second solution at 4° C. to 25° C. for at least one month.

21. The method of claim 18, further comprising freezing or lyophilizing the second solution.

* * * * *

SEQUENCE LISTING

<160> NUMBER OF SEQ ID NOS: 18

<210> SEQ ID NO 1
<211> LENGTH: 1779
<212> TYPE: DNA
<213> ORGANISM: Homo sapiens
<220> FEATURE:
<221> NAME/KEY: CDS
<222> LOCATION: (1)..(1779)
<223> OTHER INFORMATION:

<400> SEQUENCE: 1

```
atg gag ttt ggg ctg agc tgg ctt ttt ctt gtg gct att tta aaa ggt      48
Met Glu Phe Gly Leu Ser Trp Leu Phe Leu Val Ala Ile Leu Lys Gly
1               5                   10                  15 gtc cag tgt gag gtg cag ctg ttg gat tct ggg gga ggc ttg gta cag      96
Val Gln Cys Glu Val Gln Leu Leu Asp Ser Gly Gly Gly Leu Val Gln
            20                  25                  30 cct ggg ggg tgc ctg aga ctc tcc tgt gca gcc tct gga ttc acc ttt     144
Pro Gly Gly Cys Leu Arg Leu Ser Cys Ala Ala Ser Gly Phe Thr Phe
        35                  40                  45 agc agc tgt gcc atg agc tgg gtc cgc cag gct cca ggg aag ggg ctg     192
Ser Ser Cys Ala Met Ser Trp Val Arg Gln Ala Pro Gly Lys Gly Leu
    50                  55                  60 gag tgg gtc tca gct att agt ggt agt ggt ggt agc aca tac tac gca     240
Glu Trp Val Ser Ala Ile Ser Gly Ser Gly Gly Ser Thr Tyr Tyr Ala
65                  70                  75                  80 gac tcc gtg aag ggc cgg ttc acc atc tcc aga gac aaa tcc aag aac     288
Asp Ser Val Lys Gly Arg Phe Thr Ile Ser Arg Asp Lys Ser Lys Asn
                85                  90                  95 acg ttg tat ctg caa atg aac agc ctg aga gcc gag gac acg gcc gta     336
Thr Leu Tyr Leu Gln Met Asn Ser Leu Arg Ala Glu Asp Thr Ala Val
            100                 105                 110 tat tac tgt gcg aaa ggt ggc aac gat att ttg act ggt tat tat gct     384
Tyr Tyr Cys Ala Lys Gly Gly Asn Asp Ile Leu Thr Gly Tyr Tyr Ala
        115                 120                 125 tgg ggc cag gga acc ctg gtc acc gtc tca ggg agt gca tcc gcc         432
Trp Gly Gln Gly Thr Leu Val Thr Val Ser Ser Gly Ser Ala Ser Ala
    130                 135                 140 cca acc ctt ttc ccc ctc gtc tcc tgt gag aat tcc ccg tcg gat acg     480
Pro Thr Leu Phe Pro Leu Val Ser Cys Glu Asn Ser Pro Ser Asp Thr
145                 150                 155                 160 agc agc gtg gcc gtt ggc tgc ctc gca cag gac ttc ctt ccc gac tcc     528
Ser Ser Val Ala Val Gly Cys Leu Ala Gln Asp Phe Leu Pro Asp Ser
                165                 170                 175 atc act ttc tcc tgg aaa tac aag aac aac tct gac atc agc agc acc     576
Ile Thr Phe Ser Trp Lys Tyr Lys Asn Asn Ser Asp Ile Ser Ser Thr
            180                 185                 190
```

| | | |
|---|---|---|
| cgg ggc ttc cca tca gtc ctg aga ggg ggc aag tac gca gcc acc tca<br>Arg Gly Phe Pro Ser Val Leu Arg Gly Gly Lys Tyr Ala Ala Thr Ser<br>195 200 205 | | 624 |
| cag gtg ctg ctg cct tcc aag gac gtc atg cag ggc aca gac gaa cac<br>Gln Val Leu Leu Pro Ser Lys Asp Val Met Gln Gly Thr Asp Glu His<br>210 215 220 | | 672 |
| gtg gtg tgc aaa gtc cag cac ccc aac ggc aac aaa gaa aag aac gtg<br>Val Val Cys Lys Val Gln His Pro Asn Gly Asn Lys Glu Lys Asn Val<br>225 230 235 240 | | 720 |
| cct ctt cca gtg att gct gag ctg cct ccc aaa gtg agc gtc ttc gtc<br>Pro Leu Pro Val Ile Ala Glu Leu Pro Pro Lys Val Ser Val Phe Val<br>245 250 255 | | 768 |
| cca ccc cgc gac ggc ttc ttc ggc aac ccc cgc aag tcc aag ctc atc<br>Pro Pro Arg Asp Gly Phe Phe Gly Asn Pro Arg Lys Ser Lys Leu Ile<br>260 265 270 | | 816 |
| tgc cag gcc acg ggt ttc agt ccc cgg cag att cag gtg tcc tgg ctg<br>Cys Gln Ala Thr Gly Phe Ser Pro Arg Gln Ile Gln Val Ser Trp Leu<br>275 280 285 | | 864 |
| cgc gag ggg aag cag gtg ggg tct ggc gtc acc acg gac cag gtg cag<br>Arg Glu Gly Lys Gln Val Gly Ser Gly Val Thr Thr Asp Gln Val Gln<br>290 295 300 | | 912 |
| gct gag gcc aaa gag tct ggg ccc acg acc tac aag gtg acc agc aca<br>Ala Glu Ala Lys Glu Ser Gly Pro Thr Thr Tyr Lys Val Thr Ser Thr<br>305 310 315 320 | | 960 |
| ctg acc atc aaa gag agc gac tgg ctc ggc cag agc atg ttc acc tgc<br>Leu Thr Ile Lys Glu Ser Asp Trp Leu Gly Gln Ser Met Phe Thr Cys<br>325 330 335 | | 1008 |
| cgc gtg gat cac agg ggc ctg acc ttc cag cag aat gcg tcc tcc atg<br>Arg Val Asp His Arg Gly Leu Thr Phe Gln Gln Asn Ala Ser Ser Met<br>340 345 350 | | 1056 |
| tgt gtc ccc gat caa gac aca gcc atc cgg gtc ttc gcc atc ccc cca<br>Cys Val Pro Asp Gln Asp Thr Ala Ile Arg Val Phe Ala Ile Pro Pro<br>355 360 365 | | 1104 |
| tcc ttt gcc agc atc ttc ctc acc aag tcc acc aag ttg acc tgc ctg<br>Ser Phe Ala Ser Ile Phe Leu Thr Lys Ser Thr Lys Leu Thr Cys Leu<br>370 375 380 | | 1152 |
| gtc aca gac ctg acc acc tat gac agc gtg acc atc tcc tgg acc cgc<br>Val Thr Asp Leu Thr Thr Tyr Asp Ser Val Thr Ile Ser Trp Thr Arg<br>385 390 395 400 | | 1200 |
| cag aat ggc gaa gct gtg aaa acc cac acc aac atc tcc gag agc cac<br>Gln Asn Gly Glu Ala Val Lys Thr His Thr Asn Ile Ser Glu Ser His<br>405 410 415 | | 1248 |
| ccc aat gcc act ttc agc gcc gtg ggt gag gcc agc atc tgc gag gat<br>Pro Asn Ala Thr Phe Ser Ala Val Gly Glu Ala Ser Ile Cys Glu Asp<br>420 425 430 | | 1296 |
| gac tgg aat tcc ggg gag agg ttc acg tgc acc gtg acc cac aca gac<br>Asp Trp Asn Ser Gly Glu Arg Phe Thr Cys Thr Val Thr His Thr Asp<br>435 440 445 | | 1344 |
| ctg ccc tcg cca ctg aag cag acc atc tcc cgg ccc aag ggg gtg gcc<br>Leu Pro Ser Pro Leu Lys Gln Thr Ile Ser Arg Pro Lys Gly Val Ala<br>450 455 460 | | 1392 |
| ctg cac agg ccc gat gtc tac ttg ctg cca cca gcc cgg gag cag ctg<br>Leu His Arg Pro Asp Val Tyr Leu Leu Pro Pro Ala Arg Glu Gln Leu<br>465 470 475 480 | | 1440 |
| aac ctg cgg gag tcg gcc acc atc acg tgc ctg gtg acg ggc ttc tct<br>Asn Leu Arg Glu Ser Ala Thr Ile Thr Cys Leu Val Thr Gly Phe Ser<br>485 490 495 | | 1488 |
| ccc gcg gac gtc ttc gtg cag tgg atg cag agg ggg cag ccc ttg tcc<br>Pro Ala Asp Val Phe Val Gln Trp Met Gln Arg Gly Gln Pro Leu Ser<br>500 505 510 | | 1536 |

```
ccg gag aag tat gtg acc agc gcc cca atg cct gag ccc cag gcc cca      1584
Pro Glu Lys Tyr Val Thr Ser Ala Pro Met Pro Glu Pro Gln Ala Pro
        515                 520                 525 ggc cgg tac ttc gcc cac agc atc ctg acc gtg tcc gaa gag gaa tgg      1632
Gly Arg Tyr Phe Ala His Ser Ile Leu Thr Val Ser Glu Glu Glu Trp
530                 535                 540 aac acg ggg gag acc tac acc tgc gtg gtg gcc cat gag gcc ctg ccc      1680
Asn Thr Gly Glu Thr Tyr Thr Cys Val Val Ala His Glu Ala Leu Pro
545                 550                 555                 560 aac agg gtc acc gag agg acc gtg gac aag tcc acc ggt aaa ccc acc      1728
Asn Arg Val Thr Glu Arg Thr Val Asp Lys Ser Thr Gly Lys Pro Thr
            565                 570                 575 ctg tac aac gtg tcc ctg gtc atg tcc gac aca gct ggc acc tgc tac      1776
Leu Tyr Asn Val Ser Leu Val Met Ser Asp Thr Ala Gly Thr Cys Tyr
        580                 585                 590 tga                                                                  1779
```

<210> SEQ ID NO 2
<211> LENGTH: 592
<212> TYPE: PRT
<213> ORGANISM: Homo sapiens

<400> SEQUENCE: 2

```
Met Glu Phe Gly Leu Ser Trp Leu Phe Leu Val Ala Ile Leu Lys Gly
1               5                   10                  15

Val Gln Cys Glu Val Gln Leu Leu Asp Ser Gly Gly Gly Leu Val Gln
            20                  25                  30

Pro Gly Gly Cys Leu Arg Leu Ser Cys Ala Ala Ser Gly Phe Thr Phe
        35                  40                  45

Ser Ser Cys Ala Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Lys Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Gly Gly Asn Asp Ile Leu Thr Gly Tyr Tyr Ala
        115                 120                 125

Trp Gly Gln Gly Thr Leu Val Thr Val Ser Ser Gly Ser Ala Ser Ala
    130                 135                 140

Pro Thr Leu Phe Pro Leu Val Ser Cys Glu Asn Ser Pro Ser Asp Thr
145                 150                 155                 160

Ser Ser Val Ala Val Gly Cys Leu Ala Gln Asp Phe Leu Pro Asp Ser
                165                 170                 175

Ile Thr Phe Ser Trp Lys Tyr Lys Asn Asn Ser Asp Ile Ser Ser Thr
            180                 185                 190

Arg Gly Phe Pro Ser Val Leu Arg Gly Gly Lys Tyr Ala Ala Thr Ser
        195                 200                 205

Gln Val Leu Leu Pro Ser Lys Asp Val Met Gln Gly Thr Asp Glu His
    210                 215                 220

Val Val Cys Lys Val Gln His Pro Asn Gly Asn Lys Glu Lys Asn Val
225                 230                 235                 240

Pro Leu Pro Val Ile Ala Glu Leu Pro Pro Lys Val Ser Val Phe Val
                245                 250                 255
```

```
Pro Pro Arg Asp Gly Phe Phe Gly Asn Pro Arg Lys Ser Lys Leu Ile
            260                 265                 270

Cys Gln Ala Thr Gly Phe Ser Pro Arg Gln Ile Gln Val Ser Trp Leu
            275                 280                 285

Arg Glu Gly Lys Gln Val Gly Ser Gly Val Thr Thr Asp Gln Val Gln
            290                 295                 300

Ala Glu Ala Lys Glu Ser Gly Pro Thr Thr Tyr Lys Val Thr Ser Thr
305                 310                 315                 320

Leu Thr Ile Lys Glu Ser Asp Trp Leu Gly Gln Ser Met Phe Thr Cys
            325                 330                 335

Arg Val Asp His Arg Gly Leu Thr Phe Gln Gln Asn Ala Ser Ser Met
            340                 345                 350

Cys Val Pro Asp Gln Asp Thr Ala Ile Arg Val Phe Ala Ile Pro Pro
            355                 360                 365

Ser Phe Ala Ser Ile Phe Leu Thr Lys Ser Thr Lys Leu Thr Cys Leu
            370                 375                 380

Val Thr Asp Leu Thr Thr Tyr Asp Ser Val Thr Ile Ser Trp Thr Arg
385                 390                 395                 400

Gln Asn Gly Glu Ala Val Lys Thr His Thr Asn Ile Ser Glu Ser His
            405                 410                 415

Pro Asn Ala Thr Phe Ser Ala Val Gly Glu Ala Ser Ile Cys Glu Asp
            420                 425                 430

Asp Trp Asn Ser Gly Glu Arg Phe Thr Cys Thr Val Thr His Thr Asp
            435                 440                 445

Leu Pro Ser Pro Leu Lys Gln Thr Ile Ser Arg Pro Lys Gly Val Ala
450                 455                 460

Leu His Arg Pro Asp Val Tyr Leu Leu Pro Pro Ala Arg Glu Gln Leu
465                 470                 475                 480

Asn Leu Arg Glu Ser Ala Thr Ile Thr Cys Leu Val Thr Gly Phe Ser
            485                 490                 495

Pro Ala Asp Val Phe Val Gln Trp Met Gln Arg Gly Gln Pro Leu Ser
            500                 505                 510

Pro Glu Lys Tyr Val Thr Ser Ala Pro Met Pro Glu Pro Gln Ala Pro
            515                 520                 525

Gly Arg Tyr Phe Ala His Ser Ile Leu Thr Val Ser Glu Glu Glu Trp
            530                 535                 540

Asn Thr Gly Glu Thr Tyr Thr Cys Val Val Ala His Glu Ala Leu Pro
545                 550                 555                 560

Asn Arg Val Thr Glu Arg Thr Val Asp Lys Ser Thr Gly Lys Pro Thr
            565                 570                 575

Leu Tyr Asn Val Ser Leu Val Met Ser Asp Thr Ala Gly Thr Cys Tyr
            580                 585                 590

<210> SEQ ID NO 3
<211> LENGTH: 723
<212> TYPE: DNA
<213> ORGANISM: Homo sapiens
<220> FEATURE:
<221> NAME/KEY: CDS
<222> LOCATION: (1)..(723)
<223> OTHER INFORMATION:

<400> SEQUENCE: 3 atg gtg ttg cag acc cag gtc ttc att tct ctg ttg ctc tgg atc tct       48
Met Val Leu Gln Thr Gln Val Phe Ile Ser Leu Leu Leu Trp Ile Ser
1               5                  10                  15
```

```
ggt gcc tac ggg gac atc gtg atg acc cag tct cca gac tcc ctg gct      96
Gly Ala Tyr Gly Asp Ile Val Met Thr Gln Ser Pro Asp Ser Leu Ala
             20                  25                  30 gtg tct ctg ggc gag agg gcc acc atc aac tgc aag tcc agc cag agt     144
Val Ser Leu Gly Glu Arg Ala Thr Ile Asn Cys Lys Ser Ser Gln Ser
         35                  40                  45 gtt tta tac agc tcc aac aat aag aac tac tta gct tgg tac cag cag     192
Val Leu Tyr Ser Ser Asn Asn Lys Asn Tyr Leu Ala Trp Tyr Gln Gln
 50                  55                  60 aaa cca gga cag cct cct aag ctg ctc att tac tgg gca tct acc cgg     240
Lys Pro Gly Gln Pro Pro Lys Leu Leu Ile Tyr Trp Ala Ser Thr Arg
 65                  70                  75                  80 gaa tcc ggg gtc cct gac cga ttc agt ggc agc ggg tct ggg aca gat     288
Glu Ser Gly Val Pro Asp Arg Phe Ser Gly Ser Gly Ser Gly Thr Asp
                 85                  90                  95 ttc act ctc acc atc agc agc ctg cag gct gaa gat gtg gca gtt tat     336
Phe Thr Leu Thr Ile Ser Ser Leu Gln Ala Glu Asp Val Ala Val Tyr
            100                 105                 110 tac tgt cag caa tat tat agt act cct ccg acg ttc ggc caa ggg acc     384
Tyr Cys Gln Gln Tyr Tyr Ser Thr Pro Pro Thr Phe Gly Gln Gly Thr
        115                 120                 125 aag gtg gaa atc aaa cga act gtg gct gca cca tct gtc ttc atc ttc     432
Lys Val Glu Ile Lys Arg Thr Val Ala Ala Pro Ser Val Phe Ile Phe
    130                 135                 140 ccg cca tct gat gag cag ttg aaa tct gga act gcc tct gtt gtg tgc     480
Pro Pro Ser Asp Glu Gln Leu Lys Ser Gly Thr Ala Ser Val Val Cys
145                 150                 155                 160 ctg ctg aat aac ttc tat ccc aga gag gcc aaa gta cag tgg aag gtg     528
Leu Leu Asn Asn Phe Tyr Pro Arg Glu Ala Lys Val Gln Trp Lys Val
                165                 170                 175 gat aac gcc ctc caa tcg ggt aac tcc cag gag agt gtc aca gag cag     576
Asp Asn Ala Leu Gln Ser Gly Asn Ser Gln Glu Ser Val Thr Glu Gln
            180                 185                 190 gac agc aag gac agc acc tac agc ctc agc agc acc ctg acg ctg agc     624
Asp Ser Lys Asp Ser Thr Tyr Ser Leu Ser Ser Thr Leu Thr Leu Ser
        195                 200                 205 aaa gca gac tac gag aaa cac aaa gtc tac gcc tgc gaa gtc acc cat     672
Lys Ala Asp Tyr Glu Lys His Lys Val Tyr Ala Cys Glu Val Thr His
    210                 215                 220 cag ggc ctg agc tcg ccc gtc aca aag agc ttc aac agg gga gag tgt     720
Gln Gly Leu Ser Ser Pro Val Thr Lys Ser Phe Asn Arg Gly Glu Cys
225                 230                 235                 240 tag                                                                 723

<210> SEQ ID NO 4
<211> LENGTH: 240
<212> TYPE: PRT
<213> ORGANISM: Homo sapiens

<400> SEQUENCE: 4

Met Val Leu Gln Thr Gln Val Phe Ile Ser Leu Leu Trp Ile Ser
 1               5                  10                  15

Gly Ala Tyr Gly Asp Ile Val Met Thr Gln Ser Pro Asp Ser Leu Ala
             20                  25                  30

Val Ser Leu Gly Glu Arg Ala Thr Ile Asn Cys Lys Ser Ser Gln Ser
         35                  40                  45

Val Leu Tyr Ser Ser Asn Asn Lys Asn Tyr Leu Ala Trp Tyr Gln Gln
 50                  55                  60
```

Lys Pro Gly Gln Pro Pro Lys Leu Leu Ile Tyr Trp Ala Ser Thr Arg
65                  70                  75                  80

Glu Ser Gly Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln Tyr Tyr Ser Thr Pro Pro Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 5
<211> LENGTH: 480
<212> TYPE: DNA
<213> ORGANISM: Homo sapiens
<220> FEATURE:
<221> NAME/KEY: CDS
<222> LOCATION: (1)..(480)
<223> OTHER INFORMATION:

<400> SEQUENCE: 5 atg aag aac cat ttg ctt ttc tgg gga gtc ctg gcg gtt ttt att aag      48
Met Lys Asn His Leu Leu Phe Trp Gly Val Leu Ala Val Phe Ile Lys
1               5                   10                  15 gct gtt cat gtg aaa gcc caa gaa gat gaa agg att gtt ctt gtt gac      96
Ala Val His Val Lys Ala Gln Glu Asp Glu Arg Ile Val Leu Val Asp
            20                  25                  30 aac aaa tgt aag tgt gcc cgg att act tcc agg atc atc cgt tct tcc     144
Asn Lys Cys Lys Cys Ala Arg Ile Thr Ser Arg Ile Ile Arg Ser Ser
        35                  40                  45 gaa gat cct aat gag gac att gtg gag aga aac atc cga att att gtt     192
Glu Asp Pro Asn Glu Asp Ile Val Glu Arg Asn Ile Arg Ile Ile Val
    50                  55                  60 cct ctg aac aac agg gag aat atc tct gat ccc acc tca cca ttg aga     240
Pro Leu Asn Asn Arg Glu Asn Ile Ser Asp Pro Thr Ser Pro Leu Arg
65                  70                  75                  80 acc aga ttt gtg tac cat ttg tct gac ctc tgt aaa aaa tgt gat cct     288
Thr Arg Phe Val Tyr His Leu Ser Asp Leu Cys Lys Lys Cys Asp Pro
                85                  90                  95 aca gaa gtg gag ctg gat aat cag ata gtt act gct acc cag agc aat     336
Thr Glu Val Glu Leu Asp Asn Gln Ile Val Thr Ala Thr Gln Ser Asn
            100                 105                 110 atc tgt gat gaa gac agt gct aca gag acc tgc tac act tat gac aga     384
Ile Cys Asp Glu Asp Ser Ala Thr Glu Thr Cys Tyr Thr Tyr Asp Arg
        115                 120                 125

```
aac aag tgc tac aca gct gtg gtc cca ctc gta tat ggt ggt gag acc    432
Asn Lys Cys Tyr Thr Ala Val Val Pro Leu Val Tyr Gly Gly Glu Thr
        130                 135                 140 aaa atg gtg gaa aca gcc tta acc cca gat gcc tgc tat cct gac taa    480
Lys Met Val Glu Thr Ala Leu Thr Pro Asp Ala Cys Tyr Pro Asp
145                 150                 155
```

<210> SEQ ID NO 6
<211> LENGTH: 159
<212> TYPE: PRT
<213> ORGANISM: Homo sapiens

<400> SEQUENCE: 6

```
Met Lys Asn His Leu Leu Phe Trp Gly Val Leu Ala Val Phe Ile Lys
1               5                   10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155
```

<210> SEQ ID NO 7
<211> LENGTH: 24
<212> TYPE: DNA
<213> ORGANISM: Artificial
<220> FEATURE:
<223> OTHER INFORMATION: an artificially synthesized sequence

<400> SEQUENCE: 7
ccaacggcaa caaagaaaag aacg    24

<210> SEQ ID NO 8
<211> LENGTH: 24
<212> TYPE: DNA
<213> ORGANISM: Artificial
<220> FEATURE:
<223> OTHER INFORMATION: an artificially synthesized sequence

<400> SEQUENCE: 8
aacatgctct ggccgagcca gtcg    24

<210> SEQ ID NO 9
<211> LENGTH: 24
<212> TYPE: DNA
<213> ORGANISM: Artificial
<220> FEATURE:
<223> OTHER INFORMATION: an artificially synthesized sequence

```
<400> SEQUENCE: 9
gcaagtccag ccagagtgtt ttat                                          24

<210> SEQ ID NO 10
<211> LENGTH: 24
<212> TYPE: DNA
<213> ORGANISM: Artificial
<220> FEATURE:
<223> OTHER INFORMATION: an artificially synthesized sequence

<400> SEQUENCE: 10
ctgtccttgc tgtcctgctc tgtg                                          24

<210> SEQ ID NO 11
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 11
aacagctcga gccaccatgg agtttgggct gag                                33

<210> SEQ ID NO 12
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 12
agcggccagc cgccccgagc ctgtcgacag gc                                 32

<210> SEQ ID NO 13
<211> LENGTH: 32
<212> TYPE: DNA
<213> ORGANISM: Artificial
<220> FEATURE:
<223> OTHER INFORMATION: an artificially synthesized primer sequence

<400> SEQUENCE: 13
atagaattcc accatggtgt tgcagaccca gg                                 32

<210> SEQ ID NO 14
<211> LENGTH: 30
<212> TYPE: DNA
<213> ORGANISM: Artificial
<220> FEATURE:
<223> OTHER INFORMATION: an artificially synthesized primer sequence

<400> SEQUENCE: 14
ggagcaggcg gccgcacttc tccctctaac                                    30

<210> SEQ ID NO 15
<211> LENGTH: 24
<212> TYPE: DNA
<213> ORGANISM: Artificial
<220> FEATURE:
<223> OTHER INFORMATION: an artificially synthesized sequence

<400> SEQUENCE: 15
accattgaga accagatttg tgta                                          24
```

-continued

```
<210> SEQ ID NO 16
<211> LENGTH: 24
<212> TYPE: DNA
<213> ORGANISM: Artificial
<220> FEATURE:
<223> OTHER INFORMATION: an artificially synthesized sequence

<400> SEQUENCE: 16
tgtgtagcac ttgtttctgt cata                                              24

<210> SEQ ID NO 17
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 17
atgaattcca ccatgaagaa ccatttgc                                          28

<210> SEQ ID NO 18
<211> LENGTH: 26
<212> TYPE: DNA
<213> ORGANISM: Artificial
<220> FEATURE:
<223> OTHER INFORMATION: an artificially synthesized primer sequence

<400> SEQUENCE: 18
tatctagatt agtcaggata gcaggc                                            26
```